(12) United States Patent
Marks et al.

(10) Patent No.: US 6,262,200 B1
(45) Date of Patent: *Jul. 17, 2001

(54) (POLYFLUOROARYL)FLUOROANIONS OF ALUMINUM, GALLIUM, AND INDIUM OF ENHANCED UTILITY, USES THEREOF, AND PRODUCTS BASED THEREON

(75) Inventors: Tobin J. Marks, Evanston, IL (US); You-Xian Chen, Midland, MI (US)

(73) Assignee: Northwestern University, Evanston, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/329,764

(22) Filed: Jun. 10, 1999

Related U.S. Application Data

(63) Continuation-in-part of application No. 09/222,326, filed on Dec. 29, 1998, now abandoned, which is a continuation of application No. 08/912,617, filed on Aug. 18, 1997, now Pat. No. 5,854,166.
(60) Provisional application No. 60/024,190, filed on Aug. 19, 1996.

(51) Int. Cl.[7] .................................. C08F 4/99; C08F 4/02; C08F 4/60; B01J 31/00; B01J 37/00
(52) U.S. Cl. ..................... 526/127; 526/160; 526/943; 526/319; 526/346; 502/102; 502/103; 502/117; 502/153; 539/11; 539/15; 556/27; 556/28; 556/43; 556/53; 556/58; 556/187
(58) Field of Search ................................... 502/102, 103, 502/117, 153; 539/11, 15; 556/27, 28, 43, 53, 58, 187; 526/127, 160, 943

(56) References Cited

U.S. PATENT DOCUMENTS 3,928,303  12/1975  Yasui et al. ................... 260/94.3

(List continued on next page.)

FOREIGN PATENT DOCUMENTS 0416815  3/1991  (EP) .

(List continued on next page.)

OTHER PUBLICATIONS

Chen et al., ""Constrained Geometry" Dialkyl Catalysts.

(List continued on next page.)

*Primary Examiner*—Mark L. Bell
*Assistant Examiner*—J. Pasterozyk
(74) *Attorney, Agent, or Firm*—Sieberth & Patty, L.L.C.

(57) ABSTRACT

The (polyfluoroaryl)fluoroanions of aluminum, gallium, and indium are novel weakly coordinating anions which are are highly fluorinated. (Polyfluoroaryl)fluoroanions of one such type contain at least one ring substituent other than fluorine. These (polyfluoroaryl)fluoroanions of aluminum, gallium, and indium have greater solubility in organic solvents, or have a coordinative ability essentially equal to or less than that of the corresponding (polyfluoroaryl)fluoroanion of aluminum, gallium, or indium in which the substituent is replaced by fluorine. Another type of new (polyfluoroaryl) fluoroanion of aluminum, gallium, and indium have 1–3 perfluorinated fused ring groups and 2–0 perfluorophenyl groups. When used as a cocatalyst in the formation of novel catalytic complexes with d- or f-block metal compounds having at least one leaving group such as a methyl group, these anions, because of their weak coordination to the metal center, do not interefere in the ethylene polymerization process, while affecting the the propylene process favorably, if highly isotactic polypropylene is desired. Thus, the (polyfluoroaryl)fluoroanions of aluminum, gallium, and indium of this invention are useful in various polymerization processes such as are described.

30 Claims, 2 Drawing Sheets

U.S. PATENT DOCUMENTS

| | | |
|---|---|---|
| 3,950,435 | 4/1976 | Takahashi et al. ............... 260/613 R |
| 3,966,453 | 6/1976 | Takahashi et al. ..................... 71/105 |
| 5,066,741 | 11/1991 | Campbell, Jr. ........................ 526/171 |
| 5,332,706 | 7/1994 | Nowlin et al. ........................ 502/107 |
| 5,387,568 | 2/1995 | Ewen et al. ........................... 502/104 |
| 5,391,661 | 2/1995 | Naganuma et al. .................. 526/133 |
| 5,391,789 | 2/1995 | Rohrmann ............................. 556/11 |
| 5,455,366 | 10/1995 | Rohrmann ........................ 556/8 |
| 5,473,028 | 12/1995 | Nowlin et al. ........................ 526/114 |
| 5,498,581 | 3/1996 | Welch et al. .......................... 502/102 |
| 5,539,068 | 7/1996 | Devore et al. ........................ 526/126 |
| 5,554,775 | 9/1996 | Krishnamurti et al. .................. 556/7 |
| 5,582,764 | 12/1996 | Nakashima et al. ............ 252/299.61 |
| 5,599,761 | 2/1997 | Turner .................................. 502/152 |
| 5,602,067 | 2/1997 | Nowlin et al. ........................ 502/104 |
| 5,602,269 | 2/1997 | Biagini et al. ........................ 556/170 |
| 5,663,249 | 9/1997 | Ewen et al. ........................... 526/134 |
| 5,728,816 | 3/1998 | Garbassi et al. ........................ 534/15 |
| 5,734,010 | 3/1998 | Sommazzi et al. ................... 502/103 |
| 5,753,578 | 5/1998 | Santi et al. ............................. 502/114 |
| 5,756,611 | 5/1998 | Etherton et al. ...................... 526/127 |
| 5,763,549 | 6/1998 | Elder et al. ........................... 502/117 |
| 5,786,495 | 7/1998 | Resconi et al. ......................... 556/11 |
| 5,807,939 * | 9/1998 | Elder et al. ........................... 526/160 |
| 5,854,166 | 12/1998 | Marks et al. .......................... 502/153 |
| 5,939,347 * | 8/1999 | Ward et al. ........................... 526/160 |
| 6,030,918 * | 2/2000 | King et al. ............................. 526/160 |
| 6,031,145 * | 9/1998 | Commereuc et al. ................ 502/153 |

FOREIGN PATENT DOCUMENTS

| | | |
|---|---|---|
| 0427697 | 5/1991 | (EP) . |
| 0573403 | 12/1993 | (EP) . |
| 9735893 | 10/1997 | (WO) . |
| 9807515 | 2/1998 | (WO) . |
| 9832776 | 7/1998 | (WO) . |
| 9841530 | 9/1998 | (WO) . |
| 9850392 | 11/1998 | (WO) . |

OTHER PUBLICATIONS

Efficient Syntheses, C–H Bond Activation Chemistry, Monomer–Dimer Equilibration, and α–Olefin Polymerization Catalysis", Organometallics, 1997, vol. 16, No. 16, pp. 3649–3657.

Chen et al., "Sterically Encumbered (Perfluoroaryl) Borane and Aluminate Cocatalysts for Tuning Cation–Anion Ion Pair Strucucture and Reactivity in Metallocene Polymerization Processes. A Synthetic, Structural, and Polymerization Study", J. Am. Chem. Soc., 1998, vol. 120, No.25, pp. 6287–6305.

Fenton et al., "Perfluorophenyl Derivatives of the Elements II. (Pentafluorophenyl)Lithium, A Source of $_2$–Substituted Nonafluorobiphenyls", J. Organometallic Chemistry, 1964, vol. 2, pp. 437–446.

Siedle et al., "How Coordinating are Non–Coordinating Anions?", Macromol Symp., 1995, vol. 89, pp. 299–305.

Chen et al., "Very Large Counteranion Modulation of Cationic Metallocene Polymerization Activity and Stereoregulation by a Sterically Congested (Perfluoroaryl) fluoroaluminate", J. Am. Chem. Soc., 1997, vol. 119, pp. 2582–2583.

Jordan et al., J. Am. Chem. Soc., 1986, vol. 108, pp. 1718–1719.

Marks, Tobin J, "Surface–Bound Metal Hydrocarbyls. Organometallic Connections between Heterogeneous and Homogeneous Catalysts", Accounts of Chemical Research, vol. 25, No. 2, 1992, pp. 57–65.

Yang et al., "Cationic Zirconocene Olefin Polymerization Catalysts Based on the Organo–Lewis Acid Tris(pentafluorophenyl)borane. A Synthetic, Structural, Solution Dynamic, and Polymerization Catalytic Study", J. Am. Chem. Soc., 1994, vol. 116, pp. 10015–10031.

Chen et al., "Organo–Lewis Acids As Cocatalysts in Cationic Metallocene Polymerization Catalysts. Unusual Characteristics of Sterically Encumbered Tris(perfluorobiphenyl)borane", J. Am. Chem. Soc., 1996, vol. 118, pp. 12451–12452.

Chemistry, With Inorganic Qualitative Analysis, Second Edition, Therald Moeller et al, Academic Press, 1984, p 225.

* cited by examiner

(POLYFLUOROARYL)FLUOROANIONS OF ALUMINUM, GALLIUM, AND INDIUM OF ENHANCED UTILITY, USES THEREOF, AND PRODUCTS BASED THEREON

REFERENCE TO RELATED APPLICATIONS

This application is a continuation-in-part of prior application Ser. No. 09/222,326, filed Dec. 29, 1998 now abandoned, which is a continuation of application Ser. No. 08/912,617, filed Aug. 18, 1997, now U.S. Pat. No. 5,854,166, issued Dec. 29, 1998, which in turn claims priority of U.S. provisional application Ser. No. 60/024,190, filed Aug. 19, 1996. Reference is also made to commonly-owned U.S. application Ser. No. 09/328,711, filed Jun. 10, 1999.

This invention was made with Government support under Contract No. DE-FG02-86ER13511 awarded by the Department of Energy. The Government has certain rights in this invention.

BACKGROUND OF THE INVENTION

This invention relates, inter alia, to novel compositions of matter useful, inter alia, as cocatalysts, to novel catalyst compositions made using such cocatalysts, to methods for preparing these catalysts, and to methods for polymerization utilizing such catalysts.

The use of soluble Ziegler-Natta type catalysts in the polymerization of olefins is well known in the prior art. In general, such systems include a Group 4 metal compound and a metal or metalloid alkyl cocatalyst, such as aluminum alkyl cocatalyst. More broadly, it may be said to include a mixture of a Group 1, 2 or 13 metal alkyl and a transition metal complex from Group 4–5 metals, particularly titanium, zirconium, or hafnium with aluminum alkyl cocatalysts.

First generation cocatalyst systems for homogeneous metallocene Ziegler-Natta olefin polymerization, alkylaluminum chlorides ($AlR_2Cl$), exhibit low ethylene polymerization activity levels and no propylene polymerization activity. Second generation cocatalyst systems, utilizing methyl aluminoxane (MAO), raise activities by several orders of magnitude. In practice however, a large stoichiometric excess of MAO over catalyst ranging from several hundred to ten thousand must be employed to have good activities and stereoselectivities. Moreover, it has not been possible to isolate characterizable metallocene active species using MAO. The third generation of cocatalyst, $B(C_6F_5)_3$, proves to be far more efficient while utilizing a 1:1 catalyst-cocatalyst ratio. Although active catalyst species generated with $B(C_6F_5)_3$, are isolable and characterizable, the anion $MeB(C_6F_5)_3^{\ominus}$, formed after $Me^{\ominus}$ abstraction from metallocene dimethyl complexes, is weakly coordinated to the electron-deficient metal center, thus resulting in a drop of certain catalytic activities. The recently developed $B(C_6F_5)_4^{\ominus}$ type of non-coordinating anion exhibits some of the highest reported catalytic activities, but such catalysts have proven difficult to obtain in the pure state due to poor thermal stability and poor crystallizability, which is crucial for long-lived catalysts and for understanding the role of true catalytic species in the catalysis for the future catalyst design. Synthetically, it also takes two more steps to prepare such an anion than for the neutral organo-Lewis acid.

In our prior applications referred to hereinabove, and in publications appearing in *J. Am. Chem. Soc.* 1997, 119, 2582–2583, and *J. Am. Chem. Soc.* 1998, 120, 6287–6305 new, sterically encumbered (polyfluoroaryl)fluoroanions of aluminum, such as tris(perfluorobiphenyl)fluoroaluminate $(PBA)^{\ominus}$, and the preparation and use of such anions as highly efficient cocatalysts for metallocene-mediated olefin polymerization are described. The catalytically active species generated from $Ph_3C^{\oplus}PBA^{\ominus}$ are isolable and X-ray crystallographically characterizable instead of the unstable, oily residues which often result in the case of $B(C_6F_5)_4^{\ominus}$.

This invention provides, inter alia, technology described in the above-referred-to prior applications, and additionally, improvements in the technology described in the above-referred-to prior applications.

SUMMARY OF THE INVENTION

Accordingly, it is an object of the subject invention to provide, prepare and utilize new types of weakly coordinating anions which form organo-Lewis acid salts that are useful in forming novel, highly-effective olefin polymerization catalysts.

A further object of the subject invention is to provide a catalyst which permits better control over molecular weight, molecular distribution, stereoselectivity, and/or comonomer incorporation.

Another object of the subject invention is to provide a Ziegler-Natta type catalyst system which reduces the use of excess cocatalyst and activates previously unresponsive metallocenes.

In accordance with one of its embodiments, this invention provides novel (polyfluoroaryl)fluoroanions of aluminum, gallium, and indium which may be represented by the formula $$[ER'R''R'''F]^{\ominus} \qquad (I)$$

wherein E is aluminum, gallium, or indium, wherein F is fluorine, wherein R' is a fluoroaryl group having at least one additional substituent other than fluorine, wherein R" and R'" each is, independently, (i) a fluoroaryl group having at least one additional substituent other than fluorine, or (ii) a fluorinated aryl group devoid of additional substitution. Preferably, E is aluminum. In these compounds, R" and R'" are preferably the same as each other and, preferably, are fluoroaryl groups having at least one additional substituent other than fluorine. Most preferably, R' of formula (I) is the same as R" and R'". The substituent(s) other than fluorine present in the (polyfluoroaryl)fluoroanions of aluminum, gallium, and indium of formula (I) can be (i) one or more substituents which increase the solubility of the compound in an organic solvent as compared to the corresponding compound in which each such substituent other than fluorine is replaced by a fluorine atom, (ii) one or more electron withdrawing substituents other than fluorine, or (iii) a combination of at least one substituent from (i) and at least one substituent from (ii).

A second embodiment provides (polyfluoroaryl) fluoroanions of aluminum, gallium, and indium which may be referred to by the formula $$[ER'R''R'''F]^{\ominus} \qquad (II)$$

wherein E is aluminum, gallium, or indium, wherein F is fluorine, where at least one of R', R", and R'" is a fluorinated biphenyl or fluorinated polycyclic fused ring group such as naphthyl, anthracenyl or fluorenyl. E is preferably aluminum. Preferably two, and more preferably all three, of R', R", and R'" are fluorinated biphenyl or fluorinated polycyclic fused ring groups such as naphthyl, anthracenyl or fluorenyl. Two of the biphenyl groups may be replaced by a phenyl group. That is, R' is a biphenyl group and R" and R'" each is a phenyl group. The biphenyl groups and the phenyl groups plus any polycyclic fused ring group or groups of the compounds of formula (II) should be highly fluorinated, preferably with only one or two hydrogen atoms on a group, and most preferably, as in PBA$^\ominus$, with no hydrogen atoms and all fluorine substituents. Thus in one subgroup of these (polyfluoroaryl)fluoroanions, R' of formula (II) is a fluorobiphenyl group having 0 to 2 hydrogen atoms and 7 to 9 fluorine atoms on the rings thereof, the sum of the foregoing integers being 9, and R" and R'" of formula (II) each is a phenyl group having 0 to 2 hydrogen atoms and 3 to 5 fluorine atoms on the ring, the sum of the foregoing integers being 5. In this subgroup, most preferably R' is nonafluorobiphenyl and R" and R'" each is a pentafluorophenyl group, i.e., the compound is nonafluorobiphenylbis (pentafluorophenyl)fluoroaluminate. In another subgroup of these (polyfluoroaryl)fluoroanions, R' of formula (II) is a fluorobiphenyl group having 0 to 2 hydrogen atoms and 7 to 9 fluorine atoms on the rings thereof, the sum of the foregoing integers being 9, and R" and R'" of formula (II) each is a fluorinated polycyclic fused ring group such as naphthyl, anthracenyl or fluorenyl. Preferably the polycyclic fused ring group is perfluorinated. However, the fused rings may have one or two hydrogen atoms on the ring with the other available positions occupied by fluorine. A third subgroup of (polyfluoroaryl)fluoroanions of aluminum, gallium, and indium of this second embodiment are tris (fluorobiphenyl)fluoroaluminates wherein R' of formula (II) and R" and R'" of formula (II) each is a fluorobiphenyl group having 0 to 2 hydrogen atoms and 7 to 9 fluorine atoms on the rings thereof, the sum of the foregoing integers being 9, especially where such fluorobiphenyl groups are all the same as each other. The most preferred compound of this third sub-group is tris(perfluorobiphenyl)fluoroaluminate.

A third embodiment of this invention is comprised of (polyfluoroaryl)fluoroanions of aluminum, gallium, and indium of the formula:

$$[E(R^1)_n(R^2)_{3-n}F]^\ominus \quad (III)$$

wherein E is aluminum, gallium, or indium, wherein F is fluorine, wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3. Such anions include, for example:

tris(nonafluoroanthracenyl)fluoroaluminate,
bis(nonafluoroanthracenyl)(pentafluorophenyl) fluoroaluminate,
nonafluoroanthracenylbis(pentafluorophenyl) fluoroaluminate,
tris(undecafluorotetrahydronaphthyl)fluoroaluminate,
bis(undecafluorotetrahydronaphthyl)(pentafluorophenyl) fluoroaluminate,
undecafluorotetrahydronaphthylbis(pentafluorophenyl) fluoroaluminate,
tris(nonafluorofluorenyl)fluoroaluminate,
bis(nonafluorofluorenyl)(pentafluorophenyl) fluoroaluminate, and
nonafluorofluorenylbis(pentafluorophenyl) fluoroaluminate.

Anions of this embodiment in which less than half of the fluorine atoms, and preferably up to about 3 fluorine atoms, are replaced by a corresponding number of substituents other than fluorine are included within the scope of the first embodiment described above.

It will thus be seen that this invention provides various new metallic compounds in which an anion of formulas (I), (II), or (III) is paired with a suitable cation, such as an alkali metal cation, or a carbonium cation.

A fourth embodiment of this invention provides a novel complex or ion pair formed from a (polyfluoroaryl) fluoroanion of aluminum, gallium, or indium of the first embodiment. In particular, the novel complex or ion pair of this fourth embodiment comprises a cation formed from a d-block or f-block metal compound by abstraction therefrom of a leaving group (e.g., a methyl group), and formation of an ion pair comprised of a cation formed from the d-block or f-block metal compound and a (polyfluoroaryl) fluoroanion of aluminum, gallium, or indium of the formula $[ER'R"R'"F]^\ominus$. In this formula, E is aluminum, gallium, or indium, F is fluorine, R' is a fluoroaryl group having at least one additional substituent other than fluorine, and R" and R'" each is, independently, (i) a fluoroaryl group having at least one additional substituent other than fluorine, or (ii) a fluorinated hydrocarbyl group devoid of additional substitution.

A fifth embodiment of this invention provides a novel complex or ion pair formed from a (polyfluoroaryl) fluoroanion of aluminum, gallium, or indium of the third embodiment. Thus in accordance with this fifth embodiment, the complex or ion pair comprises a cation formed from a d-block or f-block metal compound by abstraction therefrom of a leaving group (e.g., a methyl group), and formation of an ion pair comprised of a cation formed from the d-block or f-block metal compound and a (polyfluoroaryl)fluoroanion of aluminum, gallium, or indium of the formula $[E(R^1)_n(R^2)_{3-n}F]^\ominus$. In this formula, E is aluminum, gallium, or indium, F is fluorine, each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), each $R^2$ is a pentafluorophenyl group, and n is 1 to 3.

In a sixth embodiment of this invention, a novel catalytic complex or ion pair is produced by a process which comprises contacting a d-block or f-block metal compound having at least one leaving group (e.g., a methyl group) with an organocation salt of a (polyfluoroaryl)fluoroanion of aluminum, gallium, or indium of the formula $[ER'R"R'"F]^\ominus$. In this formula, E is aluminum, gallium, or indium, F is fluorine, R' is a fluoroaryl group having at least one additional substituent other than fluorine, and R" and R'" each is, independently, (i) a fluoroaryl group having at least one additional substituent other than fluorine, or (ii) a fluorinated hydrocarbyl group devoid of additional substitution. In this process, which typically is conducted in a suitable anhydrous liquid solvent and in a suitably inert atmosphere or environment, a leaving group is abstracted from the d-block or f-block metal compound by the organocation, and an ion pair comprised of a cation formed from the d-block or f-block metal compound and the (polyfluoroaryl)fluoroanion of aluminum, gallium, or indium is formed to produce the catalytic complex.

A seventh embodiment is analogous to the process of the sixth embodiment except that the (polyfluoroaryl) fluoroanion of aluminum, gallium, or indium has the formula $[E(R^1)_n(R^2)_{3-n}F]^\ominus$ wherein E is aluminum, gallium, or indium, wherein F is fluorine, wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3.

An eighth embodiment of this invention is a process for polymerizing an olefinic monomer or copolymerizing two or more olefinic monomers, which process comprises contacting the monomer or monomers, preferably a single vinyl monomer or two or more copolymerizable vinyl monomers, with a polymerization catalyst complex which comprises a cation formed from a d-block or f-block metal compound by abstraction therefrom of a leaving group (e.g., a methyl group), and formation of an ion pair comprised of a cation formed from the d-block or f-block metal compound and a (polyfluoroaryl)fluoroanion of aluminum, gallium, or indium of the formula $[ER'R''R'''F]^{\ominus}$ wherein E is aluminum, gallium, or indium, wherein F is fluorine, wherein R' is a fluoroaryl group having at least one additional substituent other than fluorine, and wherein R'' and R''' each is, independently, (i) a fluoroaryl group having at least one additional substituent other than fluorine, or (ii) a fluorinated hydrocarbyl group devoid of additional substitution.

A ninth embodiment is analogous to the polymerization process of the eighth embodiment except that the (polyfluoroaryl)fluoroanion of aluminum, gallium, or indium has the formula $[E(R^1)_n(R^2)_{3-n}F]^{\ominus}$ wherein E is aluminum, gallium, or indium, wherein F is fluorine, wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3.

These and other objects, embodiments, features and advantages of this invention will be apparent from the ensuing description, appended claims, and accompanying Drawings.

Figures 2A, 2B, 2C:
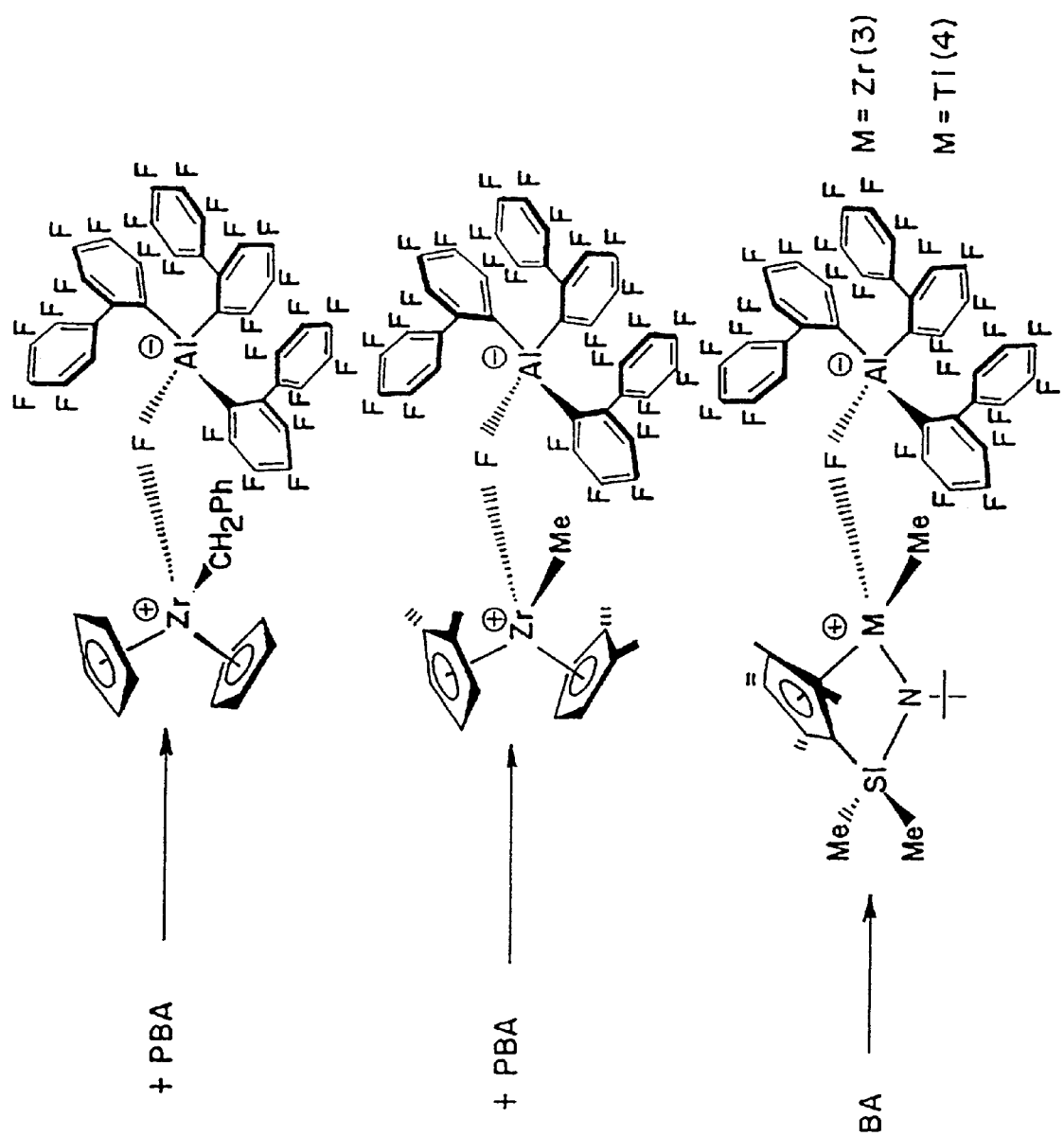
FIGS. 2a, 2b, and 2c each show a reaction pathway for a catalyst system according to the subject invention. In these Figures, $PBA=Ph_3C^{\oplus}PBA^{\ominus}$.

Pathways analogous to those depicted in FIGS. 2a–c exist when $PBA^{\ominus}$ is replaced by (a) an analogous (polyfluoroaryl) fluoroanion of aluminum, gallium, or indium of formula (I) above in which R', R'', and R''' are all the same as each other, (b) a (polyfluoroaryl)fluoroanion of aluminum, gallium, or indium of formula (II) above in which R', R'', and R''' are all the same as each other, and (c) a (polyfluoroaryl)fluoroanion of aluminum, gallium, or indium of formula (III) above in which n is 3, and all three $R^1$ groups are the same as each other.

It is to be understood that the present invention is not to be limited to any spatial configurations for complexes depicted either in the Figures or in the specification or claims of this document. Such depictions are not presented as limitations or requirements as regards stereochemical considerations, but rather are presented for purposes of illustration only.

While parts of the following discussion may focus on aluminate anions for purposes of clarity, it is equally applicable to analogous anions of gallium and indium.

FURTHER DETAILED DESCRIPTION OF THE INVENTION (Polyfluoroaryl)fluoroanions of Aluminum, Gallium, and Indium of this Invention The anions of the first, second, and third embodiments of this invention are weakly coordinating anions. When used as a cocatalyst in the formation of our novel catalyst compositions, these (polyfluoroaryl)fluoroanions, because of their weak coordination to the metal center, do not interefere in the ethylene polymerization process, while affecting the the propylene polymerization process favorably, if highly isotactic polypropylene is desired. Thus, the (polyfluoroaryl)fluoroanions of aluminum, gallium, and indium of this invention are useful in various polymerization processes such as are described.

As noted above, the novel, eminently useful (polyfluoroaryl)fluoroanions of aluminum, gallium, and indium of the first embodiment of this invention can be represented by formula (I), i.e., $[ER'R''R'''F]^{\ominus}$. In this formula, E is aluminum, gallium, or indium, F is fluorine, R' is a fluoroaryl group having at least one additional substituent other than fluorine (hereinafter sometimes called a "substituted fluoroaryl group"), and R'' and R''' each is, independently, (i) a substituted fluoroaryl group, or (ii) a fluorinated aryl group devoid of additional substitution (hereinafter sometimes called an "unsubstituted fluoroaryl group"). It will, of course, be understood that the term "substituent" in reference to the ring system of the fluoroaryl group does not include a hydrogen or deuterium atom—the substituent is something other than these. Each fluoroaryl group is highly fluorinated. Thus preferably, each substituted fluoroaryl group has (a) more fluorine atoms than such other ring substituents, (b) no more than three such other ring substituents, and at most only one hydrogen atom on the ring. More preferably, each substituted fluoroaryl group has (a) no more than two such other substituents on the ring, (b) no hydrogen atom on the ring, and (c) a fluorine atom in each of the other ring positions available for substitution. Similarly, each unsubstituted fluoroaryl group preferably contains no more than two hydrogen atoms on the ring, and more preferably no more than one hydrogen atom on the ring. Most preferably, an unsubstituted fluoroaryl group is perfluorinated.

The substituents other than fluorine on the ring(s) of R' can be, for example, one or more of the following:

hydrocarbyloxy, RO—;
hydrocarbylthio, RS—;
tri(hydrocarbyl)silyl, $R_3Si$—;
dihydrocarbylamino, $R_2N$—;
dihydrocarbylphosphino, $R_2P$—;
hydrocarbyl, R—;
trihydrocarbylsiloxy, $R_3SiO$—;
dihydrocarbyloxidoamino, $R_2N(O)$—;
dihydrocarbyloxidophosphino, $R_2P(O)$—;
poly(hydrocarbyloxy), $R(OR')_nO$—, where R' is divalent hydrocarbyl, e.g., methylene (—$CH_2$—), dimethylene (—$CH_2CH_2$—), methyldimethylene (—$CH(CH_3)CH_2$—), ethyldimethylene (—$CH(C_2H_5)CH_2$—), cyclohexylene (—$C_6H_{10}$—), phenylene (—$C_6H_4$—), or the like, and n is 1 to about 100, and preferably 1 to about 50;
poly(hydrocarbylsiloxy), $R_3SiO(R_2SiO)_nR_2SiO$—, where n is 0 to about 20); and
halide of atomic number greater than 9.

In the above formulas of the substituent groups, R, independently, is cyclic or acyclic or a group having both cyclic and acyclic portions, is saturated or contains aliphatic or aromatic unsaturation or both, and typically has no more than about 24 carbon atoms, and preferably no more than about 12 carbon atoms. In addition, the hydrocarbyl moiety of the above substituents can itself be substituted, e.g., by one or more groups such as halide, hydroxy, alkoxy, or analogous substituents. Thus the substituents other than fluorine atoms on the ring(s) of the fluoroaryl groups can be, for example, substituted hydrocarbyloxy, substituted hydrocarbylthio, substituted trihydrocarbylsilyl where 1 to 3 of the hydrocarbyls are substituted, substituted dihydrocarbylamino where one or both hydrocarbyls are substituted, substituted dihydrocarbylphosphino where one or both hydrocarbyls are substituted, substituted hydrocarbyl other than fluoroaryl, or substituted trihydrocarbylsiloxy where 1 to 3 of the hydrocarbyls are substituted.

Preferably, the (polyfluoroaryl)fluoroanion of aluminum, gallium, or indium of formula (I) is (i) a weakly coordinating anion having greater solubility in organic solvents, or (ii) a weakly coordinating anion with a coordinative ability essentially equivalent to or, more preferably, less than that of the corresponding (polyfluoroaryl)fluoroanion of aluminum, gallium, or indium in which each substituent other than fluorine is replaced by a fluorine atom. For the purposes of this invention, comparative solubility in organic solvents is measured by determining the solubility of the respective (polyfluoroaryl)fluoroanions of aluminum, gallium, and indium as salts of the same counterion in n-hexane at 20° C. Similarly, comparative coordinative ability is assessed by reacting 1,2-(9-fluorenyl)$_2C_2H_4ZrMe_2$ with a salt of the respective (polyfluoroaryl)fluoroanions of aluminum, gallium, and indium, and the $\lambda_{max}$ of the resultant [1,2-(9-fluorenyl)$_2C_2H_4ZrMe$]$^\oplus$[ER'R''R'''F]$^\ominus$complex is determined; $\lambda_{max}$ increases with decreasing anion coordination, as discussed in Siedle et al., *Macromol. Symp.*, 1995, 89, 299. The (polyfluoroaryl)fluoroanions are preferably reacted with 1,2-(9-fluorenyl)$_2C_2H_4ZrMe_2$ as salts of the same counterion; the counterion should be silver or, more preferably, a suitable organocation.

Illustrative examples of some of the preferred (polyfluoroaryl)fluoroanions of aluminum, gallium, and indium of this invention are presented in the following formulas wherein Al is aluminum, wherein F is fluorine, wherein x is 1 to 3, and wherein R is a substituent other than a fluorine atom, typically an electron-withdrawing group or a solubility-enhancing group. In formulas (IV) through (X), one or more of the fluorine atoms on the rings, typically no more than three fluorine atoms on any given fused ring structure depicted, may be replaced by such substituent(s).

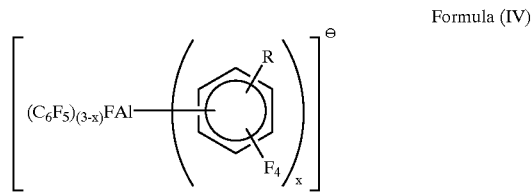

Formula (IV)

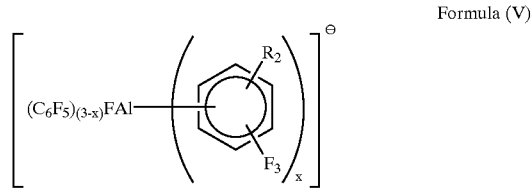

Formula (V)

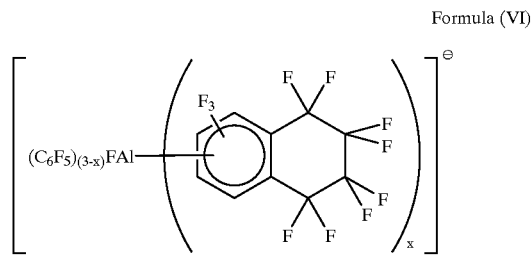

Formula (VI)

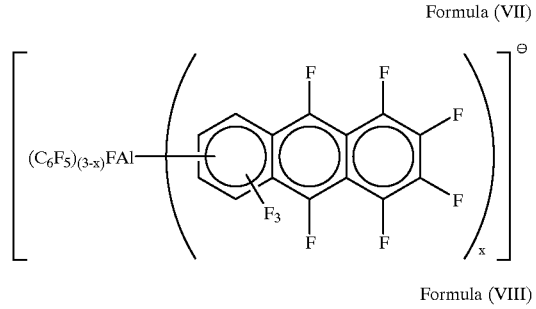

Formula (VII)

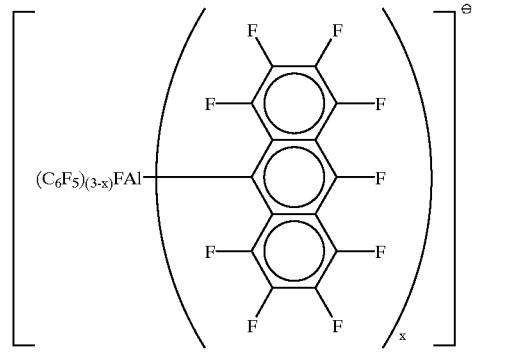

Formula (VIII)

-continued

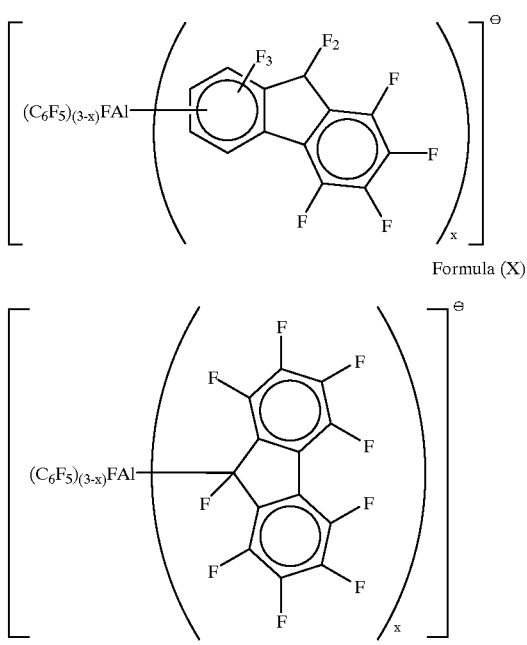

Formula (IX)

Formula (X)

The (polyfluoroaryl)fluoroanions of aluminum, gallium, and indium of this invention can be prepared by reaction between (i) an active metal derivative of the polyfluoroaromatic or substituted polyfluoroaromatic compound corresponding in structure to the structure(s) desired for R', R", and R'", or $R^1$, and if present, $R^2$, and (ii) a trihalide of aluminum, gallium, or indium. The metal of the active metal derivative is an alkali metal such as Li or Na, or a halomagnesium group, and sometimes hereinafter these cations may be referred to as main group cations. Thus, in preparing a (polyfluoroaryl)fluoroanion of aluminum, gallium, or indium of formula (I) above in which R', R", and R'" are all the same substituted fluoroaryl groups, the reaction may be depicted analogously to the scheme shown in FIG. 1.

When preparing a (polyfluoroaryl)fluoroanion of aluminum, gallium, or indium of formula (I) above wherein R' and R" each is a substituted fluoroaryl group, and R'" is a fluoroaryl group that differs therefrom (e.g., it is an unsubstituted fluoroaryl group, or it is a different substituted fluoroaryl group), a two-step reaction can be used in which the active metal derivative of R' (and R") is reacted with a trihalide of aluminum, gallium, or indium, followed by reaction of the active metal derivative of R'" with the product of the reaction between the trihalide and the active metal derivative of R' (and R"). The reverse order of these steps is also possible: the active metal derivative of R'" may be reacted with a trihalide of aluminum, gallium, or indium, and the product of this step may then be reacted with the active metal derivative of R' (and R").

Where R" and R'" each is a fluoroaryl group that is different from R', and R', R", and R'" are to differ from each other, an analogous three-step procedure is employed. Each active metal derivative is added singly and allowed to react with the trihalide of aluminum, gallium, or indium, or with the product of the previous step.

Reactions pursuant to the schemes described above can also be used for preparing (polyfluoroaryl)fluoroanions of aluminum, gallium, and indium of formula (II) above by using reactants in which R', R", and R'" are as defined in connection with formula (II). For example, $PBA^\ominus$ (FIG. 1) has been synthesized in yields as high as 72.4%. Preferred anions of formula (I) or (II) above have a coordinative ability essentially equivalent to, and preferably less than, that of $PBA^\ominus$.

Similarly, reactions pursuant to the schemes described above can be used for preparing (polyfluoroaryl)fluoroanions of aluminum, gallium, and indium of formula (III) above. In this case, R' is replaced by $R^1$, and R" and R'" are replaced by $R^2$, where $R^1$ and $R^2$ are as defined above in connection with formula (III).

Figure 1:
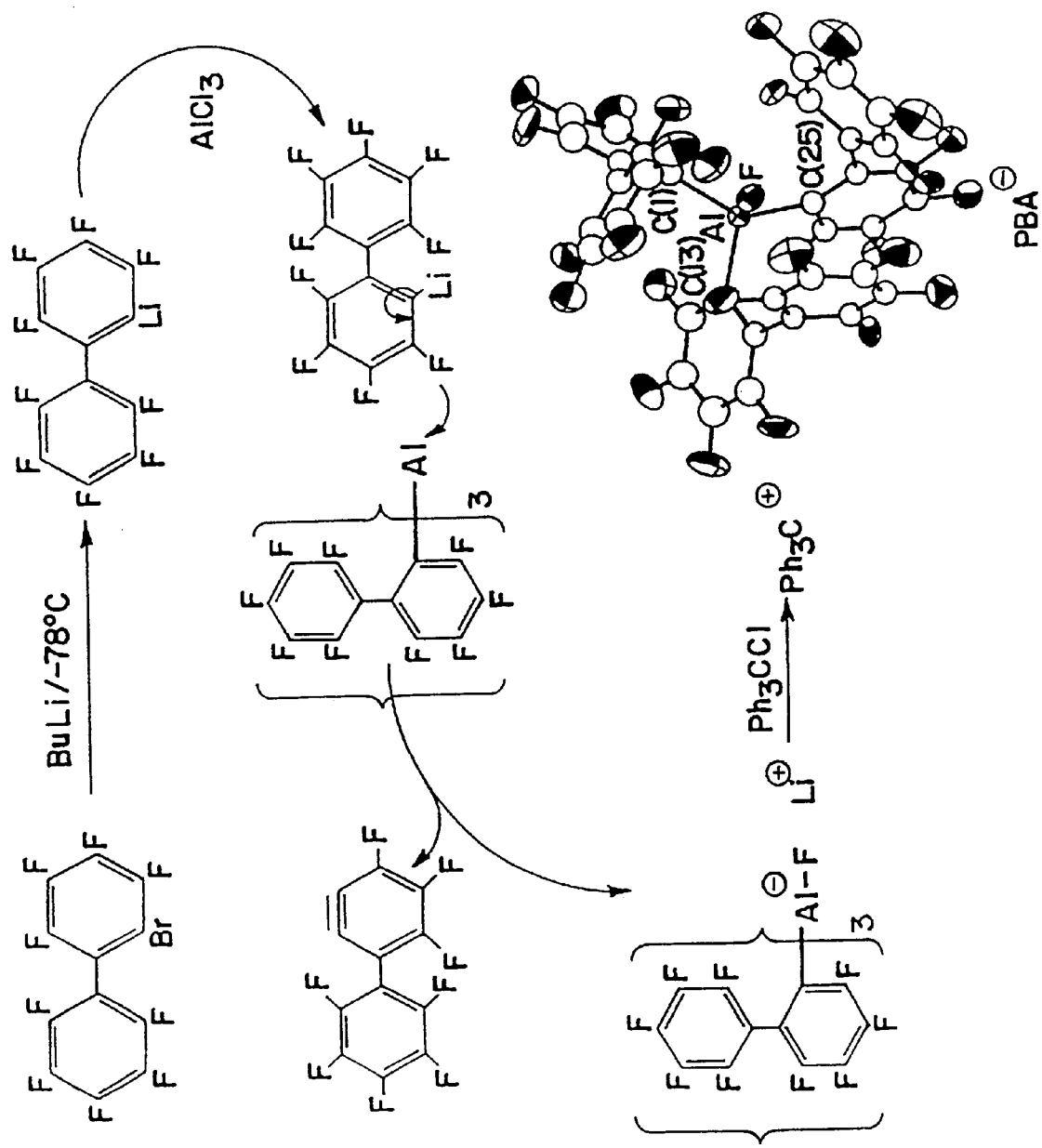
FIG. 1 is a reaction pathway for the synthesis of $PBA^{\ominus}$, which pathway is equally applicable to the synthesis of (a) analogous (polyfluoroaryl)fluoroanions of aluminum, gallium, and indium of formula (I) above in which R', R'', and R''' are all the same as each other, (b) (polyfluoroaryl) fluoroanions of aluminum, gallium, and indium of formula (II) above in which R', R'', and R''' are all the same as each other, and (c) (polyfluoroaryl)fluoroanions of aluminum, gallium, and indium of formula (III) above in which n is 3, and all three $R^1$ groups are the same as each other.

The reactions to prepare the (polyfluoroaryl)fluoroanions of aluminum, gallium, and indium of this invention are typically conducted in a suitable non-coordinating solvent such as a liquid paraffinic or aromatic hydrocarbon or a mixture thereof, and typically at temperatures in the range of about –78° C. to about 25° C. FIG. 1 and Example 1 hereinafter illustrate an overall synthesis for $PBA^\ominus$. As noted, such synthesis can readily be adapted for synthesis of (polyfluoroaryl)fluoroanions of aluminum, gallium, and indium of formulas (I), (II), and (III) above in which all three fluoroaryl groups are the same. By appropriate substitution of reactants in this procedure, a variety of such (polyfluoroaryl)fluoroanions of aluminum, gallium, and indium of this invention can be prepared.

Organocation salts of the (polyfluoroaryl)fluoroanions of this invention are usually made by metathesis of the main group cation salt of the (polyfluoroaryl)fluoroanion with a salt of the organocation, such as a chloride salt, so that the organocation salt of the (polyfluoroaryl)fluoroanion may be separated from the resultant main group metal salt. The anion of the starting organocation salt may be any convenient anion, including, but not not limited to, chloride, bromide, tetrafluoroborate, hexafluorophosphate, and the like. Preferred anions are those which facilitate the separation of the produced main group cation salt from the organocation salt of the (polyfluoroaryl)fluoroanion. A non-limiting example of this is a particularly preferrred embodiment of this invention, wherein the metathesis is conducted in a nonpolar solvent, using an organocation halide as the reactant to form a main group metal halide, which precipitates out of the nonpolar solvent, while the organocation salt of the (polyfluoroaryl)fluoroanion remains dissolved in the nonpolar solvent.

The organocations used in this invention should be chosen carefully: they generally need to be able to abstract a leaving group from a d- or f-block metal compound, and at the same time the organocation should not interact in an undesired way with the (polyfluoroaryl)fluoroanion (e.g., via fluoride abstraction). Types of organocations that may be suitable as counterions for use with the (polyfluoroaryl)fluoroanions of this invention include carbonium cations, $R_3C^\oplus$, and proton source cations, $R_3AH^\oplus$ and $R_2GH^\oplus$, where A is nitrogen, phosphorus, or arsenic, and G is oxygen or sulfur. In both the carbonium cations and the proton source cations, R is typically a hydrocarbyl group containing up to about 20 carbon atoms. Another type of cation that may be used as a counterion to the (polyfluoroaryl)fluoroanions of this invention has the formula $Cp_2M^\oplus$, in which Cp is a cyclopentadienyl-moiety-containing group and M is iron, ruthenium, osmium, or cobalt. Carbonium cations are preferred counterions; a highly preferred carbonium ion in this invention is the triphenylmethyl cation (also commonly referred to as a trityl cation).

Catalytic Complexes of this Invention

The reaction of triphenylmethyl tris(2-perfluorobiphenyl)fluoroaluminate, $[Ph_3C]^\oplus[FAl(C_{12}F_9)_3]^\ominus$, and of triphenylmethyl bis(perfluorophenyl)(2-perfluorobiphenyl) fluoroaluminate, $[Ph_3C]^{\oplus}[FAl(C_6F_5)_2(C_{12}F_9)]^{\ominus}$, with a zirconocene and other actinide or transition metal dimethyl complexes proceeds rapidly and quantitatively at room temperature in noncoordinating solvents to yield catalytic complexes. These catalytic complexes may be used in the polymerization, copolymerization, oligomerization and dimerization of a-olefins. In addition, each of these catalytic complexes may be used together with aluminum alkyls, aluminum aryls, (e.g., $AlR_3$, R=Me, Et, Ph, naphthyl) or alumoxanes (which are also known as aluminoxanes), such as methylalumoxane for increased polymer yields. This invention now makes it possible, inter alia, to synthesize a wide variety of other new catalytic complexes which can be used in the same manner for producing homopolymers, copolymers, oligomers and dimers of α-olefins. These new catalytic complexes can also be used in conjunction with hydrocarbyl aluminum compounds or alumoxanes in the efficient polymerization of various monomers of suitable, if not enhanced, properties.

Pursuant to this invention, a d- or f-block metal compound having at least one leaving group is reacted with an organocation salt of a (polyfluoroaryl)fluoroanion of aluminum, gallium, or indium of this invention whereby a leaving group is abstracted from the metal compound by the organocation, and an ion pair comprised of a cation formed from the d- or f-block metal compound and the (polyfluoroaryl)fluoroanion of aluminum, gallium, or indium is formed.

Various d- and f-block metal compounds may be used in forming the catalytically active compounds of this invention. The d-block and f-block metals of this reactant are the transition, lanthanide and actinide metals. See, for example, the Periodic Table appearing on page 225 of Moeller, et al., *Chemistry*, Second Edition, Academic Press, Copyright 1984. References herein to Groups of the Periodic Table are made with reference to the Periodic Table appearing on page 225 of Moeller et al. As regards the metal constituent, preferred are compounds of Groups 4–8 of the Periodic Table. More preferred are compounds of the metals of Groups 4–6 (Ti, Zr, Hf, V, Nb, Ta, Cr, Mo, and W) and thorium, and most preferred are thorium and the Group 4 metals, titanium and hafnium, and especially zirconium.

A vital feature of the d- or f-block metal compound used in forming the catalytic complexes of this invention is that it must contain at least one leaving group that is abstracted by an organocation, and whereby the resultant cation of the d- or f-block metal compound forms an ion pair with a (polyfluoroaryl)fluoroanion of aluminum, gallium, or indium of this invention. Univalent leaving groups that meet these criteria include hydride, hydrocarbyl free of hydrogen atoms in a β-position, and silylcarbinyl ($R_3SiCH_2$—) groups. Examples include methyl, benzyl, and trimethylsilylcarbinyl. Of these, the methyl group is the most preferred leaving group.

Metallocenes make up a preferred class of d- and f-block metal compounds used in making the catalytic complexes of this invention. These compounds are characterized by containing at least one cyclopentadienyl moiety pi-bonded to the metal atom. For use in this invention, the metallocene must also have bonded to the d- or f-block metal atom at least one leaving group capable of being abstracted by an organocation, which organocation is also a suitable counterion for the (polyfluoroaryl)fluoroanion.

Metallocene structures in this specification are to be interpreted broadly, and include structures containing 1, 2, 3 or 4 Cp or substituted Cp rings. Thus metallocenes suitable for use in this invention can be represented by the formula XI:

$$Q_aCp_bMG_cX_d \quad (XI)$$

where Cp independently in each occurrence is a cyclopentadienyl-moiety-containing group which typically has in the range of 5 to about 24 carbon atoms; Q is a bridging group or ansa group that links two Cp groups together; M is a d- or f-block metal atom; each G is, independently, a leaving group that is bonded to the d- or f-block metal atom and is capable of being abstracted by an organocation that is also a suitable counterion for the (polyfluoroaryl)fluoroanion of aluminum, gallium, or indium used in forming the catalytic complex; X is a group other than a leaving group that is bonded to the d- or f-block metal atom; a is 0 or 1; b is a whole integer from 1 to 3 (preferably 1 or 2); c is 1 to 3; d is 0 or 1; and the sum of c and d is at least 2. The sum of b, c, and d is sufficient to form a stable compound, and often is the coordination number of the d- or f-block metal atom. When using as a polymerization catalyst a complex of this invention made from a metallocene of formula (XI), X, if present, must not detrimentally affect propagation of the polymer chain during polymerization. In such case, X is preferably a hydrogen atom or a group bonded to the metal atom via a carbon atom, and most preferably, is a hydrogen atom or an alkyl group.

Cp is, independently, a cyclopentadienyl, indenyl, 4,5,6,7-tetrahydroindenyl, 1-azaindenyl, fluorenyl, or related group, including a benzo-fused indenyl and an acenaphthindenyl group as described in U. S. Pat. No. 5,455,366, or a hydrocarbyl-, halo-, halohydrocarbyl-, hydrocarbylmetalloid-, and/or halohydrocarbylmetalloid-substituted derivative of any of the foregoing groups, as long as the group can π-bond to the metal. Cp typically contains up to 75 non-hydrogen atoms. Q, if present, is typically a silylene ($>SiR_2$), benzo ($C_6H_4<$), substituted benzo, methylene (—$CH_2$—), substituted methylene, ethylene (—$CH_2CH_2$—), or substituted ethylene bridge. M is preferably a metal atom of Groups 4–8, and most preferably is thorium or a Group 4 metal atom, especially titanium, and most especially zirconium. G is the leaving group, such as hydride, or benzyl, and which in most cases is methyl. X, if present, is a non-leaving group, and thus can be a halogen atom, a non-leaving hydrocarbyl group, hydrocarbyloxy, (alkoxy, aryloxy, etc.), trihydrocarbylsiloxy, and similar univalent groups that form stable metallocenes. The sum of b, c, and d is a whole number, and is often from 3–5. When M is a Group 4 metal or an actinide metal, and b is 2, the sum of c and d is 2, c being at least 1. When M is a Group 3 or lanthanide metal, and b is 2, c is 1 and d is zero. When M is a Group 5 metal, and b is 2, the sum of c and d is 3, c being at least 2.

In one preferred group of metallocene reactants of formula (XI), b is 2, i.e., there are two cyclopentadienyl-moiety-containing groups in the molecule, and these two groups can be the same or they can be different from each other.

Also suitable for preparing catalytic complexes of this invention are compounds analogous to those of formula (XI) where one or more of the Cp groups are replaced by cyclic unsaturated charged groups isoelectronic with Cp, such as borabenzene or substituted borabenzene, azaborole or substituted azaborole, and various other isoelectronic Cp analogs. See for example Krishnamurti, et al., U.S. Pat. Nos. 5,554,775 and 5,756,611.

Another sub-group of useful metallocenes which can be used in the practice of this invention are metallocenes of the type described in WO 98/32776 published Jul. 30, 1998. These metallocenes are characterized in that one or more cyclopentadienyl groups in the metallocene are substituted by one or more polyatomic groups attached via a N, O, S, or P atom or by a carbon-to-carbon double bond. Examples of such substituents on the cyclopentadienyl ring include —OR, —SR, —NR$_2$, —CH═, —CR═, and —PR$_2$, where R can be the same or different and is a substituted or unsubstituted C$_1$–C$_{16}$ hydrocarbyl group, a tri-C$_1$–C$_8$ hydrocarbylsilyl group, a tri-C$_1$–C$_8$ hydrocarbyloxysilyl group, a mixed C$_1$–C$_8$ hydrocarbyl and C$_1$–C$_8$ hydrocarbyloxysilyl group, a tri-C$_1$–C$_8$ hydrocarbylgermyl group, a tri-C$_1$–C$_8$ hydrocarbyloxygermyl group, or a mixed C$_1$–C$_8$ hydrocarbyl and C$_1$–C$_8$ hydrocarbyloxygermyl group.

Still another subgroup of preferred metallocenes is comprised of the so-called constrained geometry metal complexes. See for example U. S. Pat. No. 5,539,068 and references cited therein at Column 1, lines 44–57. The constrained geometry complexes suitable for use in preparing catalytic complexes of this invention can be represented by the formula:

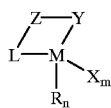

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group, n is 1 to 4, m is 0 to 3, with the sum of n plus m being 1 to 4 depending upon the valence of M. Of such compounds, preferred are those in which M is titanium or zirconium, L is a cyclopentadienyl group or a substituted cyclopentadienyl group, Z is a dihydrocarbylsilyl group, Y is a hydrocarbylamido group, R is methyl, n is 2, and m is 0. Particularly preferred compounds of this type are those in which M is titanium or zirconium, L is a tetramethylcyclopentadienyl group, Z is a dimethylsilyl group, Y is a tert-butylamido group, R is methyl, n is 2, and m is 0. The same comments regarding X as made in connection with formul (XI) above, also apply to the group designated X in the above formula. Thus, as noted above, most preferably X is a hydrogen atom or an alkyl group.

Illustrative examples of suitable d- or f-block metal compounds that can be used as reactants in forming the catalytic complexes of this invention can be found, for example, in U.S. Pat. Nos. 5,391,789; 5,498,581; 5,786,495; and in WO 98/50392 A1, published Nov. 12, 1998, provided of course that the compound contains, or is modified to contain, at least one leaving group.

Examples of metallocenes to which this invention is applicable include such compounds as:

bis(methylcyclopentadienyl)titanium dimethyl;
bis(methylcyclopentadienyl)zirconium dimethyl;
bis(n-butylcyclopentadienyl)zirconium dimethyl;
bis(dimethylcyclopentadienyl)zirconium dimethyl;
bis(diethylcyclopentadienyl)zirconium dimethyl;
bis(methyl-n-butylcyclopentadienyl)zirconium dimethyl;
bis(n-propylcyclopentadienyl)zirconium dimethyl;
bis(2-propylcyclopentadienyl)zirconium dimethyl;
bis(methylethylcyclopentadienyl)zirconium dimethyl;
bis(indenyl)zirconium dimethyl;
bis(methylindenyl)zirconium dimethyl;
dimethylsilylenebis(indenyl)zirconium dimethyl;
dimethylsilylenebis(2-methylindenyl)zirconium dimethyl;
dimethylsilylenebis(2-ethylindenyl)zirconium dimethyl;
dimethylsilylenebis(2-methyl-4-phenylindenyl) zirconium dimethyl;
1,2-ethylenebis(indenyl)zirconium dimethyl;
1,2-ethylenebis(methylindenyl)zirconium dimethyl;
2,2-propylidenebis(cyclopentadienyl)(fluorenyl) zirconium dimethyl;
dimethylsilylenebis(6-phenylindenyl)zirconium dimethyl;
bis(methylindenyl)zirconium benzyl methyl;
ethylenebis[2-(tert-butyldimethylsiloxy)-1-indenyl] zirconium dimethyl;
dimethylsilylenebis(indenyl)chlorozirconium methyl;
5-(cyclopentadienyl)-5-(9-fluorenyl)1-hexene zirconium dimethyl;
dimethylsilylenebis(2-methylindenyl)hafnium dimethyl;
dimethylsilylenebis(2-ethylindenyl)hafnium dimethyl;
dimethylsilylenebis(2-methyl-4-phenylindenyl)hafnium dimethyl;
2,2-propylidenebis(cyclopentadienyl)(fluorenyl)hafnium dimethyl;
bis(9-fluorenyl)(methyl)(vinyl)silane zirconium dimethyl,
bis(9-fluorenyl)(methyl)(prop-2-enyl)silane zirconium dimethyl,
bis(9-fluorenyl)(methyl)(but-3-enyl)silane zirconium dimethyl,
bis(9-fluorenyl)(methyl)(hex-5-enyl)silane zirconium dimethyl,
bis(9-fluorenyl)(methyl)(oct-7-enyl)silane zirconium dimethyl,
(cyclopentadienyl)(1-allylindenyl) zirconium dimethyl,
bis(1-allylindenyl)zirconium dimethyl,
(9-(prop-2-enyl)fluorenyl)(cyclopentadienyl)zirconium dimethyl,
(9-(prop-2-enyl)fluorenyl)(pentamethylcyclopentadienyl) zirconium dimethyl,
5 bis(9-(prop-2-enyl)fluorenyl) zirconium dimethyl,
(9-(cyclopent-2-enyl)fluorenyl)(cyclopentadienyl) zirconium dimethyl,
bis(9-(cyclopent-2-enyl)(fluorenyl)zirconium dimethyl,
5-(2-methylcyclopentadienyl)-5(9-fluorenyl)-1-hexene zirconium dimethyl,
1-(9-fluorenyl)-1-(cyclopentadienyl)-1-(but-3-enyl)-1-(methyl)methane zirconium dimethyl,
5-(fluorenyl)-5-(cyclopentadienyl)-1-hexene hafnium dimethyl,
(9-fluorenyl)(1-allylindenyl)dimethylsilane zirconium dimethyl,
1-(2,7-di(alpha-methylvinyl)(9-fluorenyl)-1-(cyclopentadienyl)-1,1-dimethylmethane zirconium dimethyl,
1-(2,7-di(cyclohex-1-enyl)(9-fluorenyl))-1-(cyclopentadienyl)-1,1-methane zirconium dimethyl, 5-(cyclopentadienyl)-5-(9-fluorenyl)-1-hexene titanium dimethyl,
5-(cyclopentadienyl)-5-(9-fluorenyl)1-hexene titanium dimethyl,
bis(9-fluorenyl)(methyl)(vinyl)silane titanium dimethyl,
bis(9-fluorenyl)(methyl)(prop-2-enyl)silane titanium dimethyl,
bis(9-fluorenyl)(methyl)(but-3-enyl)silane titanium dimethyl,
bis(9-fluorenyl)(methyl)(hex-5-enyl)silane titanium dimethyl,
bis(9-fluorenyl)(methyl)(oct-7-enyl)silane titanium dimethyl,
(cyclopentadienyl)(1-allylindenyl) titanium dimethyl,
bis(1-allylindenyl)titanium dimethyl,
(9-(prop-2-enyl)fluorenyl)(cyclopentadienyl)hafnium dimethyl,
(9-(prop-2-enyl)fluorenyl)(pentamethylcyclopentadienyl) hafnium dimethyl,
bis(9-(prop-2-enyl)fluorenyl) hafnium dimethyl,
(9-(cyclopent-2-enyl)fluorenyl)(cyclopentadienyl) hafnium dimethyl,
bis(9-(cyclopent-2-enyl)(fluorenyl)hafnium dimethyl,
5-(2-methylcyclopentadienyl)-5(9-fluorenyl)-1-hexene hafnium dimethyl,
5-(fluorenyl)-5-(cyclopentadienyl)-1-octene hafnium dimethyl,
(9-fluorenyl)(1-allylindenyl)dimethylsilane hafnium dimethyl.
(tert-butylamido)dimethyl(tetramethylcyclopentadienyl) silane titanium dimethyl;
(cyclopentadienyl)(9-fluorenyl)diphenylmethane zirconium dimethyl;
(cyclopentadienyl)(9-fluorenyl)diphenylmethane hafnium dimethyl;
dimethylsilanylene-bis(indenyl) thorium dimethyl;
dimethylsilanylene-bis(4,7-dimethyl-1-indenyl) zirconium dimethyl;
dimethylsilanylene-bis(indenyl) uranium dimethyl;
dimethylsilanylene-bis(2-methyl-4-ethyl-1-indenyl) zirconium dimethyl;
dimethylsilanylene-bis(2-methyl-4,5,6,7-tetrahydro-1-indenyl) zirconium dimethyl;
(tert-butylamido)dimethyl(tetramethyl-$\eta^5$-cyclopentadienyl)silane titanium dimethyl;
(tert-butylamido)dimethyl(tetramethyl-$\eta^5$-cyclopentadienyl)silane chromium dimethyl;
(tert-butylamido)dimethyl(tetramethyl-$\eta^5$-cyclopentadienyl)silane titanium dimethyl; and
(phenylphosphido)dimethyl(tetramethyl-$\eta^5$-cyclopentadienyl)silane titanium dimethyl.

In many cases the metallocenes such as referred to above will exist as racemic mixtures, but pure enantiomeric forms or mixtures enriched in a given enantiomeric form can be used.

A few illustrative examples of catalytically active catalytic complexes of this invention include the following, wherein $[Al(R^1)_n(R^2)_{3-n}F]^\ominus$ is a moiety corresponding to a (polyfluoroaryl)fluoroaluminate anion of any of formulas (IV) to (X), above.

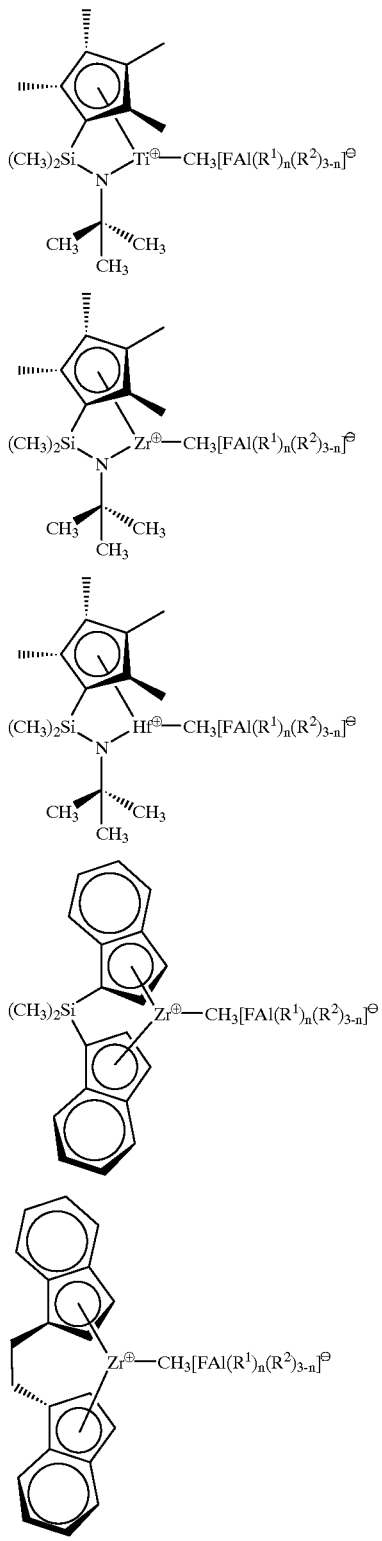

The equations presented below illustrate some of the reactions used in forming the new catalytic complexes of this invention. In these equations, Cp represents a cyclopentadienyl-moiety-containing group. Other abbreviations used in various portions of this document include the following:

| | |
|---|---|
| $C_5H_5$ | = $\eta^5$-cyclopentadienyl |
| $C_5H_3Me_2$ | = $\eta^5$-dimethylcyclopentadienyl |
| $C_5H_3(SiMe_3)_2$ | = $\eta^5$-bis(trimethylsilyl)cyclopentadienyl |
| $C_5Me_5$ | = $\eta^5$-pentamethylcyclopentadienyl |
| Ind | = $\eta^5$-$C_9H_7$ (indenyl) |
| Flu | = $\eta^5$-$C_{13}H_9$ (fluorenyl) |

More particularly, reaction of a (polyfluoroaryl)fluoroanion of aluminum, gallium, or indium of formula (I) above with a Group 4 dimethyl at temperatures in the range of about −78° C. to about 25° C. proceeds cleanly to yield cationic complexes such as set forth below.

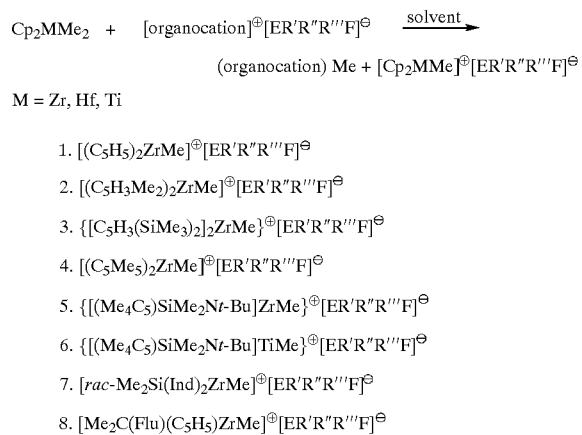

$M = Zr, Hf, Ti$

1. $[(C_5H_5)_2ZrMe]^{\oplus}[ER'R''R'''F]^{\ominus}$
2. $[(C_5H_3Me_2)_2ZrMe]^{\oplus}[ER'R''R'''F]^{\ominus}$
3. $\{[C_5H_3(SiMe_3)_2]_2ZrMe\}^{\oplus}[ER'R''R'''F]^{\ominus}$
4. $[(C_5Me_5)_2ZrMe]^{\oplus}[ER'R''R'''F]^{\ominus}$
5. $\{[(Me_4C_5)SiMe_2Nt\text{-}Bu]ZrMe\}^{\oplus}[ER'R''R'''F]^{\ominus}$
6. $\{[(Me_4C_5)SiMe_2Nt\text{-}Bu]TiMe\}^{\oplus}[ER'R''R'''F]^{\ominus}$
7. $[rac\text{-}Me_2Si(Ind)_2ZrMe]^{\oplus}[ER'R''R'''F]^{\ominus}$
8. $[Me_2C(Flu)(C_5H_5)ZrMe]^{\oplus}[ER'R''R'''F]^{\ominus}$ Other types of cationic metallocene catalyst systems can also be created with the (polyfluoroaryl)fluoroanions of aluminum, gallium, and indium of this invention such as depicted in formulas (I), (II), and (III) above. For example, metallocene cations of mono-Cp type can be formed by the reaction of mono(pentamethylcp) trimethyl Group 4 complexes with $Ph_3C^{\oplus}PBA^{\ominus}$. When $PBA^{\ominus}$ is replaced in these reactions by a (polyfluoroaryl)fluoroanion of aluminum, gallium, or indium of formula (I), the product contains an ion pair comprised of a cation formed from the mono (pentamethylcp) trimethyl Group 4 complex and a (polyfluoroaryl)fluoroanion of aluminum, gallium, or indium.

Constrained geometry types of zirconocene and titanocene cations, such as those in FIG. 2c where M=Zr or Ti, are readily produced by the reaction of the corresponding dimethyl metallocenes with (polyfluoroaryl)fluoroanions of aluminum, gallium, and indium of formulas (I), (II), and (III).

The following Examples are presented for purposes of illustration. They are not intended to limit, and should not be construed as limiting, the scope of this invention to the particulars set forth therein.

EXPERIMENTAL

Materials and Methods

All manipulations of air-sensitive materials were performed with rigorous exclusion of oxygen and moisture in flamed Schlenk-type glassware on a dual-manifold Schlenk line or interfaced to a high-vacuum line ($10^{-6}$ Torr), or in a nitrogen-filled Vacuum Atmospheres glovebox with a high capacity recirculator (1–2 ppm $O_2$). Argon (Matheson, prepurified) and ethylene (Matheson, polymerization grade) were purified by passage through a supported MnO oxygen-removal column and an activated Davison 4 Å molecular sieve column. Ether solvents were purified by distillation from Na/K alloy/benzophenone ketyl. Hydrocarbon solvents (toluene, pentane) were distilled under nitrogen from Na/K alloy. All solvents for vacuum line manipulations were stored in vacuo over Na/K alloy in Teflon-valved bulbs. Deuterated solvents were obtained from Cambridge Isotope Laboratories (all ≧99 atom % D), and were freeze-pump-thaw degassed, dried over Na/K alloy, and stored in resealable flasks. Non-halogenated solvents were dried over Na/K alloy and halogenated solvents were distilled over $P_2O_5$ and stored over activated Davison 4 Å molecular sieves. $BrC_6F_5$ (Aldrich) was vacuum distilled over $P_2O_5$. $AlCl_3$, $Ph_3CCl$ and n-BuLi (1.6M in hexanes) were purchased from Aldrich.

Physical and Analytical Measurements

NMR spectra were recorded on either Varian VXR 300 (FT 300 MHz, $^1H$; 75 MHz, $^{13}C$) or Varian Germini-300 (FT 300 MHz, $^1H$; 75 MHz, $^{13}C$; 282 MHz, $^{19}F$) instruments. Chemical shifts for $^1H$ and $^{13}C$ spectra were referenced using internal solvent resonances and are reported relative to tetramethylsilane. $^{19}F$ NMR spectra were referenced to external $CFCl_3$. NMR experiments on air-sensitive samples were conducted in Teflon valve-sealed sample tubes (J. Young). Melting temperatures of polymers were measured by DSC (DSC 2920, TA Instruments, Inc.) from the second scan with a heating rate of 20° C./min.

EXAMPLE 1

Synthesis of Triphenylmethyl tris (perfluorobiphenyl)fluoroaluminate, $Ph_3C^{\oplus}PBA^{\ominus}$ a) n-Butyllithium (1.6M in hexanes, 25 mL, 40 mmol) was added dropwise to bromopentafluorobenzene (18.0 g, 9.1 mL, 72.9 mmol) in 100 mL of diethyl ether cooled by a cold-water bath. The mixture was then stirred for a further 12 hours at room temperature. Removal of the solvent followed by vacuum sublimation at 60–65° C./$10^{-4}$ Torr gave 12.0 g of 2-bromononafluorobiphenyl as a white crystalline solid, a yield of 83.3%. $^{19}F$ NMR ($C_6D_6$, 23° C.): −126.77 (d, $^3J^{F-F}$=25.4 Hz, 1 F, F-3), −135.13 (d, $^3J_{F-F}$=18.9 Hz, 1 F, F-6), −138.85 (d, $^3J_{F-F}$=17.2 Hz, 2 F, F-2'/F-6'), −148.74 (t, $^3J_{F-F}$=20.8 Hz, 1 F, F-4), −150.13 (t, $^3J_{F-F}$=21.7 Hz, 1 F, F-4'), −154.33 (t, $^3J_{F-F}$=21.4 Hz, 1 F, F-5), −160.75 (t, $^3J_{F-F}$=23.9 Hz, 2 F, F-3'/F-5').

b) 13.2 mL of n-butyllithium (1.6M in hexanes, 21.0 mmol) was gradually added to the above 2-bromononafluorobipyhenyl (8.29 g, 21.0 mmol) in a mixed solvent of 70 mL of diethyl ether and 70 mL of pentane at −78° C. The mixture was stirred for an additional 2 h, and aluminum trichloride (0.67 g, 5.0 mmol) was then quickly added. The mixture was stirred at −78° C. for 1 hour, and the temperature was then allowed to slowly rise to room temperature. A white suspension resulted after stirring for an additional 12 hours. The mixture was filtered and the solvent was removed from the filtrate in vacuo. 100 mL of pentane was added to the sticky yellow residue and the mixture was stirred for 1 hour. The resulting white solid was collected by filtration and dried in vacuo to give 3.88 g of tris(2,2',2''-nonafluorobiphenyl)$_3$FAl$^{\ominus}$Li$^{\oplus}$·OEt$_2$, a yield of 72.4%. $^1H$ NMR ($C_7D_8$, 23° C.): 2.84 (q, J=7.2 Hz, 4 H, 2-$CH_2O$), 0.62

(t, J=7.2 Hz, 6 H, 2CH$_3$CH$_2$O—). $^{19}$F NMR (C$_6$D$_6$, 23° C.): −122.80 (s, br, 3 F, F-3), −134.86 (s, 3 F, F-6), −139.12 (s, 6 F, F-2'/F-6'), −153.95 (t, $^3J_{F-F}$=18.3 Hz, 3 F, F-4), −154.52 (t, $^3J_{F-F}$=20.2 Hz, 6 F, F-4'/F-5), −162.95 (s, 6 F, F-3'/F-5'), −176.81 (s, br, 1 F, Al—F). The above lithium salt (1.74 g, 1.62 mmol) and Ph$_3$CCl (0.48 g, 1.72 mmol) were suspended in pentane and stirred overnight. The resulting orange solid was collected by filtration and washed with pentane. The crude product is then redissolved in CH$_2$Cl$_2$ and filtered through Celite to remove LiCl, followed by pentane addition to precipitate the orange solid. Recrystallization from CH$_2$Cl$_2$/pentane at −78° C. overnight gave 1.56 g of orange crystals of the title compound, a yield of 70.5%. Analytical and spectroscopic data for Ph$_3$C$^⊕$PBA$^⊖$ are as follows: $^1$H NMR (CDCl$_3$, 23° C.): 8.25 (t, J=7.5 Hz, 3 H, p-H, Ph), 7.86 (t, J=7.5 Hz, 6 H, m-H, Ph), 7.64 (dd, J=8.4 Hz, J=1.2 Hz, 6 H, o-H, Ph), 1.28 (m), 0.88(t) (pentane residue). $^{19}$F NMR (CDCl$_3$, 23° C.): −121.05 (s, 3 F, F-3), −139.81 (s, 3 F, F-6), −141.19 (s, 6 F, F-2'/F-6), −156.93 (t, $^3J_{F-F}$=18.3 Hz, 6 F, F-4/F-4'), −158.67 (s, 3 F, F-5), −165.32 (s, 6 F, F-3'/F-5'), −175.60 (s, br, 1 F, Al—F). Analysis: calculated for C$^{60}$H$_{15}$AlF$_{28}$, C$_5$H$_{12}$: C, 57.12; H, 1.99; found: C, 57.16; H, 1.43.

EXAMPLE 2

Synthesis of [(C$_5$H$_5$)$_2$ZrCH$_2$Ph]$^⊕$[PBA]$^⊖$ (C$_5$H$_5$)$_2$Zr(CH$_2$Ph)$_2$ (0.081 g, 0.20 mmol) and Ph$_3$C$^⊕$PBA$^⊖$ (0.261 g, 0.20 mmol) were charged in the glove box into a 25-mL reaction flask with a filter frit and the flask was reattached to the high vacuum line. Toluene (15 mL) was then vacuum-transferred into this flask at −78° C. The mixture was slowly allowed to warm to room temperature and stirred for 4 hours. The volume of toluene was reduced to 5 mL, and 10 mL of pentane was then condensed into the flask at −78° C. The suspension which formed was quickly filtered and the orange crystalline solid which was collected was dried under vacuum overnight. 0.22 g were obtained for a yield of 84.4%. Large orange crystals were obtained by slowly cooling a pentane solution of the compound to −20° C. over a period of several days. $^1$H NMR (C$_6$D$_6$, 23° C.): 6.95 (t, J=7.8 Hz, 2 H, m-H, Ph), 6.80 (t, J=7.5 Hz, 1 H, p-H, Ph), 6.46 (d, J=7.2 Hz, 2 H, o-H, Ph), 5.45 (s, 5 H, Cp), 5.42 (s, 5 H, Cp), 2.47 (d, J=11.4 Hz, 1 H, —CH$_2$), 1.92 (d, J=11.4 Hz, 1 H, —CH$_2$). $^{19}$F NMR (C$_6$D$_6$, 23° C.): −117.09 (t, $^3J_{F-F}$=20.5 Hz, 3 F), −133.17 (t, $^3J_{F-F}$=15.2 Hz, 3 F), −138.60 (d, $^3J_{F-F}$=27.3 Hz, 3 F), −139.53 (t, $^3J_{F-F}$=21.2 Hz, 3 F), −146.34 (s, br, 1 F, Al—F), −152.01 (t, $^3J_{F-F}$=24.3 Hz, 3 F), −153.15 (t, $^3J_{F-F}$=20.9 Hz, 3 F), −153.92 (t, $^3J_{F-F}$=18.3 Hz, 3 F), −160.82 (d, $^3J_{F-F}$=21.4 Hz, 3 F), −162.52 (t, $^3J_{F-F}$=24.53 Hz, 3 F), $^{13}$C NMR (C$_7$D$_8$, 23° C.): 130.23 (s, ipso-Ph), 129.20 (d, $^3J_{CH}$=156.2 Hz, Ph), 128.26 (d, $^3J_{CH}$=157.1 Hz, Ph), 125.42 (d, J$_{CH}$=158.1 Hz, Ph), 125.42 (d, $^3J_{CH}$=158.1 Hz, Ph), 114.77 (d, $^3J_{CH}$=176.5 Hz, Cp), 66.68 (t, $^3J_{CH}$=122.8 Hz, —CH$_2$), Analysis: calculated for C$_{53}$H$_{17}$AlF$_{28}$Zr: C, 48.82; H, 1.31; found: C, 48.77; H, 1.36.

EXAMPLE 3

Synthesis of [Cp$_2$ZrMe]$^⊕$[PBA]$^⊖$ (Cp=C$_5$H$_3$Me$_2$ or C$_5$H$_3$(SiMe$_3$)$_2$)

3(a) Cp=C$_5$H$_3$Me$_2$. The procedure of Example 2 was used to prepare this species; the yield is 81.7%. $^1$H NMR (C$_2$D$_2$Cl$_4$, 23° C.): δ 5.95 (s, br, 1 H, C$_5$H$_3$Me$_2$), 5.77 (s, br, 1 H, C$_5$H$_3$Me$_2$), 5.72 (s, br, 1 H, C$_5$H$_3$Me$_2$), 5.46 (s, br, 1 H, C$_5$H$_3$Me$_2$), 5.70 (s, br, 1 H, C$_5$H$_3$Me$_2$), 5.40 (s, br, 1 H, C$_5$H$_3$Me$_2$), 2.11 (s, 3 H, C$_5$H$_3$Me$_2$), 1.98 (s, 3 H, C$_5$H$_3$Me$_2$), 1.76 (s, 3 H, C$_5$H$_3$Me$_2$), 1.70 (s, 3 H, C$_5$H$_3$Me$_2$), 0.28 (d, $^1J_{CH}$=120.3 Hz, Zr—$^{13}$CH$_3$). $^{19}$F NMR (C$_2$D$_2$Cl$_4$, 23 ° C.) is similar to that of the product of Example 2 except for a different chemical shift for the bridging F at −143.38 ppm. Analysis: calculated for C$_{51}$H$_{21}$AlF$_{28}$Zr: C, 47.71; H, 1.65; found: C, 47.46; H, 1.37.

3(b) Cp=C$_5$H$_3$(SiMe$_3$)$_2$. The procedure of Example 2 was repeated using [C$_5$H$_3$(SiMe$_3$)$_2$]$_2$ZrMe$_2$. The product decomposes in toluene solution within 2 hours at 25° C. and undergoes rapid decomposition to a myriad of unidentified products at higher temperatures. Characterization of the complex is based on very clean NMR scale reactions. This complex was generated in situ for polymerization studies. $^1$H NMR (C$_7$D$_8$, 23° C.): δ 6.88 (s, br, 1 H, C$_5$H$_3$(SiMe$_3$)$_2$), 6.71 (t, J=2.1 Hz, 1 H, C$_5$H$_3$(SiMe$_3$)$_2$), 6.31 (s, br, 1 H, C$_5$H$_3$(SiMe$_3$)$_2$), 6.23 (s, br, 1 H, C$_5$H$_3$(SiMe$_3$)$_2$), 5.79 (s, br, 1 H, C$_5$H$_3$(SiMe$_3$)$_2$), 5.71 (s, br, 1 H, C$_5$H$_3$(SiMe$_3$)$_2$), 0.70 (s, br, 3 H, Zr—CH$_3$), 0.17 (s, 3 H, C$_5$H$_3$(SiMe$_3$)$_2$), 0.10 (s, 3 H, C$_5$H$_3$(SiMe$_3$)$_2$), −0.05 (s, 3 H, C$_5$H$_3$(SiMe$_3$)$_2$), −0.07 (s, 3 H, C$_5$H$_3$(SiMe$_3$)$_2$). $^{19}$F NMR (C$_7$D$_8$, 23° C.): δ −112.12 (d, $^3J_{F-F}$=12.2 Hz, 3 F), −133.22 (t, $^3J_{F-F}$=15.5 Hz, 3 F), −137.49 (s, 3 F), −138.40 (t, $^3J_{F-F}$=21.7 Hz, 3 F), −144.23 (s, br, 1 F, Al—F), −153.41 (m, 6 F), −154.15 (t, $^3J_{F-F}$=21.2 Hz, 3 F), −161.80 (d, $^3J_{F-F}$=18.3 Hz, 3 F), −162.82 (t, $^3J_{F-F}$=21.4 Hz, 3 F).

EXAMPLE 4

[(C$_5$Me$_5$)$_2$ZrMe]$^⊕$[PBA]$^⊖$

[(C$_5$Me$_5$)$_2$ZrMe]$^⊕$[PBA]$^⊖$ is too thermally unstable at 25° C. to isolate. The $^1$H NMR monitored reaction of (C$_5$Me$_5$)$_2$ZrMe$_2$ and Ph$_3$C$^⊕$PBA$^⊖$ in C$_2$D$_2$Cl$_4$ clearly reveals the formation of Ph$_3$CCH$_3$ (δ 2.15) and a broad singlet at δ0.25 assignable to the ZrCH$_3$$^⊕$ group. More than 4 Cp methyl resonances at δ1.97–1.72 ppm with different intensities are observed, indicating decomposition. This complex was generated in situ for polymerization studies. $^{19}$F NMR (C$_2$D$_2$Cl$_4$): δ −114.77 (s, br, 3 F), −132.11 (t, $^3J_{F-F}$=15.2 Hz, 3 F), −136.84 (t, $^3J_{F-F}$=22.0 Hz, 3 F), −137.29 (s, br, 3 F), −150.90 (t, $^3J_{F-F}$=20.9 Hz, 3 F), −151.85 (t, $^3J_{F-F}$=23.9 Hz, 3 F), −152.47 (t, $^3J_{F-F}$=24.5 Hz, 3 F), −155.78 (s, br, 1 F Al—F), −160.02 (d, $^3J_{F-F}$=16.5 Hz, 3 F), −161.06 (t, $^3J_{F-F}$=21.2 Hz, 3 F).

EXAMPLE 5

Synthesis of [Me$_2$Si($^t$BuN)(C$_5$Me$_4$)MMe]$^⊕$[PBA]$^⊖$ (M=Zr or Ti)

5(a) M=Zr. Me$_2$Si(Me$_4$C$_5$)($^t$BuN)ZrMe$_2$ (0.148 g, 0.4 mmol) and Ph$_3$C$^⊕$PBA$^⊖$ (0.523, 0.4 mmol) were reacted in the same manner as in Example 2 to yield 0.35 g of the above complex as a white crystalline solid, a yield of 64.8%. The complex is quite soluble in pentane and cold pentane was used to wash the product. Two diastereomers are found in a 2.9:1 ratio. $^1$H NMR (C$_7$D$_8$, 23° C.) for diastereomer A (74%): δ 1.98 (s, 3 H, C$_5$Me$_4$), 1.82 (s, 3 H, C$_5$Me$_4$), 1.76 (s, 3 H, C$_5$Me$_4$), 1.27 (s, 3 H, C$_5$Me$_4$), 0.93 (s, 9 H, N—$^t$Bu), 0.24 (s, 3 H, SiMe$_2$), 0.18 (s, 3 H, SiMe$_2$), 0.15 (s, 3 H, Zr—CH$_3$). Diastereomer B (26%): δ 2.01 (s, 3 H, Me$_4$C$_5$), 1.92 (s, 3 H, Me$_4$C$_5$), 1.73 (s, 3 H, Me$_4$C$_5$), 1.24 (s, 3 H, Me$_4$C$_5$), 1.24 (s, 3 H, Me$_4$C$_5$), 0.93 (s, 9 H, N—$^t$Bu), 0.34 (s, 3 H, Zr—CH$_3$), 0.24 (s, 3 H, SiMe$_2$), 0.18 (s, 3 H, SiMe$_2$). $^{19}$F NMR (C$_7$D$_8$, 23° C.) for diastereomer A (74%): δ −−108.92 (s, br, 1 F, Al—F), −117.26 (s, br, 3 F), −133.19 (t, $^3J_{F-F}$=12.1 Hz, 3 F), −139.25 (s, 6 F), −152.53 (t, $J_{F-F}$=21.2 Hz, 3 F), −153.00 (d, $^3J_{F-F}$=21.2 Hz, 3 F), −153.00 (d, $^3J_{F-F}$=21.4 Hz, 3 F), −153.76 (t, $^3J_{F-F}$=24.3 Hz, 3 F), −160.94 (t, $^3J_{F-F}$=22.6 Hz, 3 F), −162.80 (t, $^3J_{F-F}$=21.4 Hz, 3 F). $^{13}$C NMR (C$_7$D$_8$, 23° C.) for diastereomer A (74%): δ 130.19 (C$_5$Me$_4$), 128.09 (C$_5$Me$_4$), 127.18 (C$_5$Me$_4$), 126.44 (C$_5$Me$_4$), 124.33 (C$_5$Me$_4$), 56.63 (N—CMe$_3$), 40.70 38.58 (q, J=120.6 Hz, Zr—CH$_3$), 32.70 (q, J=120.8 Hz, N—CMe$_3$), 15.75 (q, J=127.9 Hz, C$_5$Me$_4$), 14.05 (q, J=128.0 Hz, C$_5$Me$_4$), 12.00 (q, J=127.8 Hz, C$_5$Me$_4$), 10.18 (q, J=128.1 Hz, C$_5$Me$_4$), 8.49 (q, J=121.0 Hz, SiMe$_2$), 6.52 (q, J=120.9 Hz, SiMe$_2$). Analysis: calculated for C$_{52}$H$_{30}$AlF$_{28}$NSiZr: C, 46.37; H, 2.25; N, 1.04; found: C, 46.65; H, 2.13; N, 0.89.

5(b) M=Ti. The procedure of Example 2 was repeated using Me$_2$Si(Me$_4$C$_5$)($^t$BuN)TiMe$_2$ (0.065 g, 0.2 mmol) and Ph$_3$C$^⊕$PBA$^⊖$ (0.261, 0.2 mmol) to yield 0.12 g of the above complex as a yellow crystalline solid, a yield of 46.0%. Due to its good solubility in pentane, a significant amount of the product remained in the filtrate, resulting in a low isolated yield. An NMR scale reaction indicates the formation of the compound in quantitative yield when isolation is not required. Two diastereomers are found in a 3.3:1 ratio. $^1$H NMR (C$_6$D$_6$, 23° C.) for diastereomer A (77%): δ 2.01 (s, 3 H, C$_5$Me$_4$), 1.72 (s, 3 H, C$_5$Me$_4$), 1.61 (s, 3 H, C$_5$Me$_4$), 1.20 (s, 3 H, C$_5$Me$_4$), 0.93 (s, 9 H, N—$^t$Bu), 0.75 (d, J=3.9 Hz, 3 H), 0.21 (s, H), 0.06 (s, 3 H). Diastereomer B (23%): δ 1.76 (s, 3 H, Me$_4$C$_5$), 1.65 (s, 3 H, Me$_4$C$_5$), 1.57 (s, 3 H, Me$_4$C$_5$), 1.17 (s, 3 H, Me$_4$C$_5$), 0.96 (s, 9 H N—$^t$Bu), 0.79 (d, br, 3 H, Ti—CH$_3$), 0.31 (s, 3 H, SiMe$_2$), 0.09 (s, 3 H, SiMe$_2$). $^{19}$F NMR is similar to that of 3 except for slightly different chemical shifts. Analysis: calculated for C$_{52}$H$_{30}$AlF$_{28}$NSiTi: C, 47.91; H, 2.32; N, 1.07; found: C, 47.47; H, 1.96; N, 0.87.

EXAMPLE 6

Synthesis of [Me$_2$Si(Ind)$_2$ZrMe]$^⊕$[PBA]$^⊖$

The procedure of Example 2 was repeated, using Me$_2$Si (Ind)$_2$ZrMe$_2$ (0.082 g, 0.20 mmol) and Ph$_3$C$^⊕$PBA$^⊖$ (0.261, 0.20 mmol) to yield 0.19 g of the title complex as an orange crystalline solid, a 68.6% yield. Two diastereomers are found in a 1.3:1 ratio. $^1$H NMR (C$_6$D$_6$, 23° C.) for diastereomer A (56%): δ 7.45 (d, J=8.7 Hz, 1 H, C$_6$—HO, 7.27–6.88 (m, 4 H, C$_6$—H), 6.67 (t, J=7.5 Hz, 2 H, C$_6$—H), 5.88 (t, J=7.5 Hz, 1 H, C$_6$—H), 6.82 (t, J=3.3 Hz, 1 H, C$_5$-β H), 5.96 (d, J=3.3 Hz, 1 H, C$_5$-β H), 5.69 (s, br, 1 H, C$_5$-α H), 5.19 (d, J$_{HF}$=2.1 Hz, 3 H, Zr—CH$_3$). Diastereomer B (44%): δ 7.94 (d, J=8.7 Hz, 1 H, C$_6$—H), 7.27–6.88 (m, 4 H, C$_6$—H), 6.58 (t, J=7.5 Hz, 2 H, C$_6$—H), 5.79 (t, J=7.5 H, C$_6$—H), 6.42 (d, J=3.3 Hz, 1 H, C$_5$-β H), 5.85 (d, J=3.3 Hz, 1 H, C$_5$-β H), 5.56 (s, br, 1 H, C$_5$-α H), 4.80 (d, J=3.3 Hz, 1 H, C$_5$-α H), 0.46 (s, 3 H, SiMe$_2$), 0.25 (s, 3 H, SiMe$_2$), −0.64 (d, J$_{HF}$=2.1 Hz, 3 H, Zr—CH$_3$). $^{19}$F NMR (C$_6$D$_6$, 23° C.) for diastereomer A (56%): δ −115.86 (s, br, 3 F), −132.23 (s, br, 1 F, Al—F), −133.76 (t, $^3J_{F-F}$=18.3 Hz, 3 F), −138.53 (s, br, 3 F), −139.40 (t, $^3J_{F-F}$=18.3 Hz, 3 F), −153.10 (t, $^3J_{F-F}$=18.3 Hz, 3 F), −153.44 (t, $^3J_{F-F}$=18.3 Hz, 3 F), −154.72 (t, $^3J_{F-F}$=21.2 Hz, 3 F), −161.18 (t, $^3J_{F-F}$=18.3 Hz, 3 F), −162.86 (t, $^3J_{F-F}$=18.3 Hz, 3 F). Diastereomer B (44%): δ −113.48 (s, br, 3 F), −133.76 (t, $^3J_{F-F}$=21.2 Hz, 3 F), −134.44 (s, br, 1 F, Al—F), −137.89 (s, br, 3 F), −139.09 (t, $^3J_{F-F}$=18.3 Hz, 3 F), −153.10 (t, $^3J_{F-F}$=18.3 Hz, 3 F), −153.28 (t, $^3J_{F-F}$=18.3 Hz, 3 F), −153.73 (t, $^3J_{F-F}$=18.3 Hz, 3 F), −161.03 (t, $^3J_{F-F}$=18.3 Hz, 3 F), −162.68 (t, $^3J_{F-F}$=18.3 Hz, 3 F). $^{13}$C NMR (C6D$_6$, 23° C.): δ 134.02, 132.96, 132.43, 128.31, 127.67, 127.28, 126.95, 126.64, 126.21, 125.90, 125.81, 124.88, 124.20, 124.10, 123.57, 122.89, 122.01, 121.98 (C$_6$-ring), 119.16, 116.56, 115.96, 114.94, 112.90, 112.79 (C$_5$-ring), 91.82, 90.95, 89.30, 89.20, (C$_5$—Si), 51.46, 51.73, (Zr—CH$_3$), −1.31, −2.13, −2.88, −3.51 (SiMe$_2$). Analysis: calculated for C$_{57}$H$_{21}$AlF$_{28}$SiZr: C, 49.47; H, 1.53; found: C, 49.09; H, 1.27.

EXAMPLE 7

Synthesis of [Me$_2$C(Flu)(C$_5$H$_4$)ZrMe]$^⊕$[PBA]$^⊖$

Me$_2$C(Flu)(C$_5$H$_4$)Zr(CH$_3$)$_2$ (3.9 mg, 0.010 mmol) and Ph$_3$C$^⊕$PBA$^⊖$ (13.1 mg, 0.010 mmol) are added to a J. Young NMR tube and toluene-d$_8$ is condensed into the tube. The mixture is allowed to react at room temperature for 0.5 hour before the NMR spectrum was recorded. A pair of diastereomers was formed in a 1.7:1 ratio. The C$_6$H$_4$ signals of the fluorenyl region could not be assigned due to overlap between the signals of the two isomers as well as with those of triphenylethane. $^1$H NMR (C$_7$D$_8$, 23° C.) for diastereomer A: δ 6.20 (d, J$_{H-H}$=2.7 Hz, 1 H, C$_5$H$_4$), 5.44 (d, J$_{H-H}$=2.7 Hz, 1 H, C$_5$H$_4$), 4.84 (d, J$_{H-H}$=2.7 Hz, 1 H, C$_5$H$_4$), 4.61 (d, J$_{H-H}$=2.7 Hz, 1 H, C$_5$H$_4$), 1.60 (s, 3 H, CMe$_2$), 1.43 (s, 3 H, CMe$_2$), −1.03 (s, 3 H, Zr—CH$_3$). Diastereomer B: δ 6.32 (d, J$_{H-H}$=2.7 Hz, 1 H, C$_5$H$_4$), 5.21 (d, J$_{H-H}$=2.7 Hz, 1 H, C$_5$H$_4$), 4.98 (d, J$_{H-H}$=2.7 Hz, 1 H, C$_5$H$_4$), 4.56 (d, J$_{H-H}$=2.7 Hz, 1 H, C$_5$H$_4$), 1.65 (s, 3 H, CMe$_2$), 1.49 (s, 3 H, CMe$_2$), −1.07 (s, 3 H, Zr—CH$_3$). $^{19}$F NMR (C$_7$D$_8$, 23° C.): δ −−115.99 (m, br), −131.32 (s, br, Al—F), −133.31 (s, br, Al—F), −134.08 (m), −138.56 (m), −139.54 (m), −153.55 (m), −154.69 (m), −155.08 (m), −161.24 (t, $^3J_{F-F}$=18.0 Hz), −162.98 (t, $^3J_{F-F}$=26.1 Hz).

Analogous catalytic complexes of this invention are formed when Examples 2–7 are repeated using chemically equivalent amounts of organocation salts of (polyfluoroaryl) fluoroanions of aluminum, gallium, and indium of formula (I), or of formula (II), or of formula (III), in place of the (polyfluoroaryl)fluoroaluminate salt used in Examples 2–7.

Polymerization Reactions and Supported Cocatalysts of this Invention

The catalytic complexes of this invention are effective for use as catalysts for producing in variety of homopolymers and copolymers. When employed as catalysts, the catalytic complexes of this invention can be used in solution or deposited on a solid support. When used in solution polymerization, the solvent can be, where applicable, a large excess quantity of the liquid olefinic monomer. Typically, however, an ancillary inert solvent, typically a liquid paraffinic or aromatic hydrocarbon solvent is used, such as heptane, isooctane, decane, toluene, xylene, ethylbenzene, mesitylene, or mixtures of liquid paraffinic hydrocarbons and/or liquid aromatic hydrocarbons. When the catalytic complexes of this invention are supported on a carrier, the solid support or carrier can be any suitable particulate solid, and particularly a porous support such as talc, one or more zeolites, or one or more inorganic oxides, or a resinous support material such as a polyolefin. Preferably, the support material is an inorganic oxide in finely divided form.

Suitable inorganic oxide support materials which are desirably employed include metal oxides such as silica, alumina, silica-alumina and mixtures thereof. Other inorganic oxides that may be employed either alone or in combination with the silica, alumina or silica-alumina are magnesia, titania, zirconia, and like metal oxides. Such support materials can be treated with a suitable reagent such as an alumoxane (e.g., methylalumoxane) or an alkylaluminum compound (e.g., an aluminum trialkyl such as triethylaluminum). Other suitable support materials are finely divided polyolefins such as finely divided polyethylene.

In a preferred embodiment of this invention there is provided a supported cocatalyst composition comprising an organocation salt of a (polyfluoroaryl)fluoroanion of aluminum, gallium, or indium of formula (I), formula (II), or formula (III) above supported on a carrier such as described above, and especially on a porous support such as talc, a zeolite, or one or inorganic oxides, most preferably a porous silica. Such compositions are of advantage in that such supported cocatalysts can be provided to various end users for carrying out polymerization reactions using their own respective preferred d- or f-block metal-containing catalyst. All that is required is for the end user to contact the selected d- or f-block metal-containing compound having at least one leaving group with the supported organocation salt of the (polyfluoroaryl)fluoroanion of aluminum, gallium, or indium of this invention in the presence of a suitable solvent or diluent so that the catalytic complex is formed on and/or in the pores of the support, thereby forming a supported catalyst of this invention.

Another preferred embodiment of this invention is a supported catalyst composition comprising a catalytic complex of this invention formed from d- or f-block metal-containing compound having at least one leaving group, and a (polyfluoroaryl)fluoroanion of aluminum, gallium, or indium of formula (I), formula (II), or formula (III) above, supported on a carrier such as described above, and especially on a porous support such as talc, a zeolite, or one or more inorganic oxides, most preferably a porous silica.

In preparing the supported (polyfluoroaryl)fluoroanion of aluminum, gallium, or indium cocatalysts of this invention, an organocation salt of the (polyfluoroaryl)fluoroanion of aluminum, gallium, or indium of this invention can be added to and mixed with a slurry of the support in a suitable anhydrous inert liquid diluent so that the cocatalyst is deposited on the support. Agitation and heat can be utilized in performing this operation. After the deposition has occurred, the treated support is isolated and dried under an inert atmosphere to prepare a supported cocatalyst of this invention. Such supported dried cocatalyst should be kept under an inert atmosphere or in an anhydrous inert diluent under an inert atmosphere until the use of the supported cocatalyst in forming an active catalyst composition, a step which typically will be conducted in situ immediately prior to initiation of a polymerization reaction pursuant to this invention. Another preferred way of forming the supported (polyfluoroaryl)fluoroanion of aluminum, gallium, or indium cocatalyst compositions of this invention is to employ the incipient impregnation technique described in U.S. Pat. Nos. 5,332,706 and 5,473,028. In utilizing this technique, a supported catalyst is formed by contacting a porous silica having a known total pore volume with a solution of an organocation salt of a (polyfluoroaryl) fluoroanion of aluminum, gallium, or indium of formula (I), (II), or (III) above, the volume of the solution being equal to or less than such total pore volume so that the solution impregnates the silica and is thus disposed within the body of the resultant dry particles. In U.S. Pat. No. 5,602,067 this concept is expanded to using an even larger volume of the solution, provided the volume of the solution is less than required for forming a slurry of the catalyst particles in the solution, and this procedure can be adapted for use with the organocation salts of (polyfluoroaryl)fluoroanions of aluminum, gallium, and indium of formulas (I), (II), and (III) above in lieu of the aluminoxanes referred to in the patent.

To prepare the supported catalyst compositions of this invention, the procedures described in the immediately preceding paragraph can be utilized with the exception that in addition to an organocation salt of a (polyfluoroaryl) fluoroanion of aluminum, gallium, or indium of formula (I), (II), or (III) above, a d- or f-block metal compound having at least one leaving group is used so that the metal compound, the organocation, and the (polyfluoroaryl) fluoroanion of aluminum, gallium, or indium interact with each other to produce the active catalytic complex which is supported on and/or in the pores of the support. Thus use can be made of any catalyst slurry deposition procedure, or the incipient impregnation procedures of U.S. Pat. Nos. 5,332, 706 and 5,473,028, or the procedure of U.S. Pat. No. 5,602,067 involving use of a volume of treating solution in excess of the total pore volume but less than the volume required for forming a slurry of the catalyst particles in the solution of the catalyst.

Polymers can be produced pursuant to this invention by homopolymerization of polymerizable olefins, typically 1-olefins (also known as α-olefins) such as ethylene, propylene, 1-butene, styrene, or copolymerization of two or more copolymerizable monomers, at least one of which is typically a 1-olefin. The other monomer(s) used in forming such copolymers can be one or more different 1-olefins and/or a diolefin, and/or a polymerizable acetylenic monomer. Olefins that can be polymerized in the presence of the catalysts of this invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Normally, the hydrocarbon monomers used, such as 1-olefins, diolefins and/or acetylene monomers, will contain up to about 10 carbon atoms per molecule. Preferred 1-olefin monomers for use in the process include ethylene, propylene, 1-butene, 3-methyl-1-butene, 4-methyl-1-pentene, 1-hexene, and 1-octene. It is particularly preferred to use supported or unsupported catalysts of this invention in the polymerization of ethylene, or propylene, or ethylene and at least one $C_3$–$C_8$ 1-olefin copolymerizable with ethylene. Typical diolefin monomers which can be used to form terpolymers with ethylene and propylene include butadiene, hexadiene, norbornadiene, and similar copolymerizable diene hydrocarbons. 1-Heptyne and 1-octyne are illustrative of suitable acetylenic monomers which can be used. Often the monomer or monomers being polymerized comprise(s) a 1-olefin, a vinylaromatic monomer, or an ester of acrylic or methacrylic acid.

The catalytic complexes of this invention can also be used for producing homopolymers and copolymers of certain functionally-substituted monomers or mixtures of monomers in which at least one monomer is a functionally-substituted monomer. One such group of functionally-substituted monomers which can be homopolymerized or copolymerized pursuant to this invention is comprised of monomers of the formula:

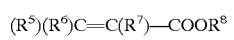

wherein $R^5$, $R^6$, and $R^7$, are, independently hydrogen atoms or hydrocarbyl groups typically having up to about 20 carbon atoms, such as alkyl or aryl groups, and $R^8$ is a hydrocarbyl group such as an alkyl or aryl group having up to about 20 carbon atoms. When $R^5$, $R^6$, and/or $R^7$ are hydrocarbyl groups, each one present preferably is an alkyl group containing from 1 to 4 carbon atoms. Most preferably $R^5$ is a methyl group, $R^6$ is a hydrogen atom or methyl group, and $R^7$ is a hydrogen atom.

Polymerization of ethylene or copolymerization with ethylene and an α-olefin having 3 to 10 carbon atoms may be performed in either the gas or liquid phase (e.g. in a solvent, such as toluene, or heptane). The polymerization can be conducted at conventional temperatures (e.g., 0° to 120° C.) and pressures (e.g., ambient to 50 kg/cm$^2$) using conventional procedures as to molecular weight regulations and the like.

The heterogeneous catalysts of this invention can be used in polymerizations conducted as slurry processes or as gas phase processes. By "slurry" is meant that the particulate catalyst is used as a slurry or dispersion in a suitable liquid reaction medium which may be composed of one or more ancillary solvents (e.g., liquid aromatic hydrocarbons, etc.) or an excess amount of liquid monomer to be polymerized in bulk. Generally speaking, these polymerizations are conducted at one or more temperatures in the range of about 0 to about 160° C., and under atmospheric, subatmospheric, or superatmospheric conditions. Conventional polymerization adjuvants, such as hydrogen, may be employed if desired. Preferably polymerizations conducted in a liquid reaction medium containing a slurry or dispersion of a catalyst of this invention are conducted at temperatures in the range of about 40 to about 110° C. Typical liquid diluents for such processes include hexane, toluene, and like materials. Typically, when conducting gas phase polymerizations, superatmospheric pressures are used, and the reactions are conducted at temperatures in the range of about 50 to about 160° C. These gas phase polymerizations can be performed in a stirred or fluidized bed of catalyst in a pressure vessel adapted to permit the separation of product particles from unreacted gases. Thermostated ethylene, comonomer, hydrogen and an inert diluent gas such as nitrogen can be introduced or recirculated to maintain the particles at the desired polymerization reaction temperature. An aluminum alkyl such as triethylaluminum may be added as a scavenger of water, oxygen and other impurities. In such cases, the aluminum alkyl is preferably employed as a solution in a suitable dry liquid hydrocarbon solvent such as toluene or xylene. Concentrations of such solutions in the range of about $5 \times 10^{-5}$ molar are conveniently used. Solutions of greater or lesser concentrations can be used, if desired. Polymer product can be withdrawn continuously or semi-continuously at a rate that maintains a constant product inventory in the reactor.

Because of the high activity and productivity achievable by use of catalysts of this invention, the catalyst levels used in olefin polymerizations can be less than previously used in typical olefin polymerizations conducted on an equivalent scale. In general, the polymerizations and copolymerizations conducted pursuant to this invention are carried out using a catalytically effective amount of a novel catalyst composition of this invention, which amount may be varied depending upon such factors such as the type of polymerization being conducted, the polymerization conditions being used, and the type of reaction equipment in which the polymerization is being conducted. In many cases, the amount of the catalyst of this invention used will be such as to provide in the range of about 0.000001 to about 0.01 percent by weight of d- or f-block metal based on the weight of the monomer(s) being polymerized.

After polymerization and deactivation of the catalyst in a conventional manner, the product polymer can be recovered from the polymerization reactor by any suitable means. When conducting the process with a slurry or dispersion of the catalyst in a liquid medium the product typically is recovered by a physical separation technique (e.g. decantation, etc.). The recovered polymer is usually washed with one or more suitably volatile solvents to remove residual polymerization solvent or other impurities, and then dried, typically under reduced pressure with or without addition of heat. When conducting the process as a gas phase polymerization, the product after removal from the gas phase reactor is typically freed of residual monomer by means of a nitrogen purge, and often can be used without further catalyst deactivation or catalyst removal.

When preparing polymers pursuant to this invention, conditions may be used for preparing unimodal or multimodal polymer types. For example, mixtures of catalysts of this invention formed from two or more different metallocenes having different propagation and termination rate constants for ethylene polymerizations can be used in preparing polymers having broad molecular weight distributions of the multimodal type.

The following Examples of polymerizations conducted pursuant to this invention are presented for purposes of illustration and not limitation.

EXAMPLES 8–17

Ethylene and Propylene Polymerization

In a glove box, a flamed 250 mL 3-necked round-bottom flask equipped with a magnetic stirring bar was charged with metallocene (5–10 mg) and cocatalyst $Ph_3C^{\oplus}PBA^{\ominus}$, in a 1:1 molar ratio and the flask was then reattached to the high vacuum line. A measured amount of dry toluene (50 mL for this study) was next condensed onto the solids and the mixture was warmed to room temperature with stirring for 10 minutes to preactivate the catalyst. The resulting solution was then equilibrated at desired reaction temperature using an external constant temperature bath. Gaseous ethylene or propylene was next introduced with rapid stirring and the pressure was maintained at 1.0 atm by means of a mercury bubbler. After a measured time interval, the reaction was quenched by the addition of 2% acidified methanol. The polymer was collected by filtration, washed with methanol, and dried on a high vacuum line overnight to a constant weight. Highly isotactic polypropylene is the result of using $PBA^{\ominus}$ as the weakly coordinating anion. The conditions and results of these polymerizations are summarized in the Table.

TABLE

Polymerization Results for Metallocenes Activated with $Ph_3C^{\oplus}PBA^{\ominus}$

| Ex. No. | Metallocene | Monomer | Tp (° C.) | µmol of cat. | Reaction time (min) | Polymer yields (g) | Activity[b] (g polymer/mol of cat · amt · h) | $M_w$[c] | $M_w/M_n$ | $T_m$[d] (° C.) | $\Delta H_\mu$ (cal/g) |
|---|---|---|---|---|---|---|---|---|---|---|---|
| 8 | $(C_5H_5)_2ZrMe_2$ | ethylene | 25 | 20 | 20 | 0 | 0 | | | | |
| 9 | $(C_5H_3Me_2)_2ZrMe_2$ | ethylene | 25 | 20 | 30 | 0.18 | $1.80 \times 10^4$ | $5.46 \times 10^5$ | 6.0 | 139.4 | 40.5 |
| 10 | $[C_5H_3(SiMe_3)_2]_2ZrMe_2$ | ethylene | 25 | 15 | 2.0 | 0.54 | $1.08 \times 10^6$ | $1.26 \times 10^6$ | 5.6 | 142.3 | 29.5 |

TABLE-continued

Polymerization Results for Metallocenes Activated with $Ph_3C^{\oplus}PBA^{\ominus}$

| Ex. No. | Metallocene | Monomer | Tp (°C.) | μmol of cat. | Reaction time (min) | Polymer yields (g) | Activity[b] (g polymer/mol of cat · amt · h) | $M_w$[c] | $M_w/M_n$ | $T_m$[d] (°C.) | $\Delta H_\mu$ (cal/g) |
|---|---|---|---|---|---|---|---|---|---|---|---|
| 11 | $(C_5Me_5)_2ZrMe_2$ | ethylene | 25 | 15 | 0.67 | 1.15 | $6.90 \times 10^6$ | $8.97 \times 10^4$ | 4.6 | 138.0 | 53.9 |
| 12 | $Me_2Si(Me_4C_5)(^tBuN)ZrMe_2$ | ethylene | 25 | 15 | 10 | 0 | 0 | | | | |
| 13 | $Me_2Si(Me_4C_5)(^tBuN)TiMe_2$ | ethylene | 25 | 15 | 10 | 0 | 0 | | | | |
| 14 | $Me_2Si(Me_4C_5)(^tBuN)TiMe_2$ | ethylene | 60 | 30 | 30 | 0.20 | $1.33 \times 10^4$ | $2.05 \times 10^6$ | 3.9 | 139.2 | 19.5 |
| 15 | $Me_2Si(Me_4C_5)(^tBuN)TiMe_2$ | ethylene | 110 | 30 | 5.0 | 0.20 | $8.00 \times 10^4$ | $2.05 \times 10^6$ | 3.1 | 142.5 | 24.4 |
| 16 | rac-$Me_2Si(Ind)_2ZrMe_2$ | propylene | 60 | 20 | 120 | 0.65 | $1.63 \times 10^4$ | $6.97 \times 10^4$ | 2.4 | 145.0 | — |
| 17 | rac-$Me_2Si(Ind)_2ZrMe_2$[e] | propylene | 60 | 2 | 1.5 | 0.93 | $1.90 \times 10^7$ | $4.11 \times 10^4$ | 2.2 | 127 | — |

[a]Reproducibility between runs = 10–15%
[b]Carried out at 1 atm of ethylene and 50 mL of toluene on high vacuum line
[c]GPC relative to polystyrene standards
[d]DSC from the second scan
[e]Comparative run; activated with $Ph_3C^{\oplus}B(C_6F_5)_4^{\ominus}$ The table summarizes polymerization activities for various metallocene catalysts activated with $Ph_3C^{\oplus}PBA^{\ominus}$. $(C_5H_5)_2ZrMe_2$ exhibits virtually no activity for ethylene polymerization. This is presumably caused by anion coordination through the Zr—F—Al bridge (FIG. 2a). However, as the ligand framework of the cation portion changes from $C_5H_5$ to 1,2,—$Me_2C_5H_3$ to 1,3—$(SiMe_3)_2C_5H_3$ to $C_5Me_5$, the activity for ethylene polymerization increases dramatically (Examples 8–11) and reaches the highest level of $6.90 \times 10^6$ g of PE/(mole of cat-atm-h) when $(C_5Me_5)_2ZrMe_2$ is the metallocene used to form the catalyst (Example 11). The polyethylene produced is highly linear, with a melting temperature Tm of 138.0° C., and crystalline, with a heat of fusion $\Delta H\mu$ of 53.9 cal/g. As the bulkiness of cation portion increases, the degree of anion coordination drops significantly, clearly reflecting the relationship between the polymerization activity and the relative tightness of cation-anion pairing in the structure.

In the case of the $C_5Me_5$ ligand, the separation of cation and anion reaches an optimum condition for reactivity that results in the maximum polymerization activity and instability of the cationic complex derived therefrom as well. Such a dramatic influence of the ligand framework substituents on polymerization activity is unprecedented, and suggests the special features of the subject anion. $PBA^{\ominus}$ is apparently such a large anion that separation of anion and cation can be easily and substantially tuned and optimized by selecting the appropriate bulky cation.

For the sterically more accessible $Me_2Si(Me_4C_5)(^tBuN)$-ligated catalysts, $PBA^{\ominus}$ promotes no catalytic activity at room temperature, a result of strong anion coordination, which is reflected by the 66 ppm down-field shift of the Al—F F resonance as compared to $PBA^{\ominus}$ (FIG. 2c, Examples 12 and 13). However, as the temperature of polymerization increases, the polymerization activity increases dramatically (Examples 12–15), presumably due to a higher degree of separation of cation-anion pairs at higher temperatures.

For the polymerization of propylene (Examples 16–17), [rac-$Me_2Si(Ind)_2ZrMe]^{\oplus}[B(C_6F_5)_4]^{\ominus}$ produces polypropylene of low isotacticity, [mmmm]=84%, while [rac-$Me_2Si(Ind)_2ZrMe]^{\oplus}[PBA]^{\ominus}$ yields highly isotactic polypropylene ([mmmm]=98%), though at a somewhat lower activity than the $[B(C_6F_5)_4]^{\ominus}$ analogue. The x-ray crystal structure of [rac-$Me_2Si(Ind)_2ZrMe]^{\oplus}[PBA]^{\ominus}$ (see *J. Am. Chem. Soc.* 1998, 120, 6287–6305) shows a strongly ion-paired $[PBA]^{\ominus}$ anion, which coordinatively "intrudes" into the cation coordination sphere, and may account for both the enhancement in stereoselectivity and the decrease in polymerization activity towards propylene.

Compounds referred to by chemical name or formula anywhere in this document, whether referred to in the singular or plural, are identified as they exist prior to coming into contact with another substance referred to by chemical name or chemical type (e.g., another component, a solvent, etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Each and every patent or publication referred to in any portion of this specification is incorporated in toto into this disclosure by reference, as if fully set forth herein.

This invention is susceptible to considerable variation in its practice. Therefore the is foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for polymerizing a polymerizable olefinic monomer or copolymerizing two or more copolymerizable olefinic monomers, which process comprises contacting said monomer or monomers with a polymerization catalyst complex which comprises a cation formed from a d-block or f-block metal compound by abstraction therefrom of a leaving group, and formation of an ion pair comprised of a cation of said d-block or f-block metal compound and a (polyfluoroaryl)fluoroanion of aluminum, gallium, or indium of the formula:

[ER'R"R'"F]$^{\ominus}$ wherein E is aluminum, gallium, or indium, wherein F is fluorine, wherein R' is a fluoroaryl group having at least one additional substituent other than fluorine, wherein R" and R'" each is, independently, (i) a fluoroaryl group having at least one additional substituent other than fluorine, or (ii) a fluorinated hydrocarbyl group devoid of additional substitution.

2. A process of claim or 1 wherein said monomer or monomers comprise(s) a 1-olefin, a vinylaromatic monomer, or an ester of acrylic or methacrylic acid.

3. A process of claim 1 wherein said metal compound is a metallocene represented by the formula:

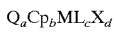

where Cp independently in each occurrence is a cyclopentadienyl-moiety-containing group which has in the range of 5 to about 24 carbon atoms; Q is a bridging group or ansa group that links two Cp groups together; M is a d- or f-block metal atom; each L is, independently, a leaving group that is bonded to the d- or f-block metal atom and is capable of being abstracted by an organocation of the organocation salt of the (polyfluoroaryl)fluoroanion used in forming the catalytic complex; X is a group other than a leaving group that is bonded to the d- or f-block metal atom and does not detrimentally affect propagation of the polymer chain during polymerization; a is 0 or 1; b is a whole integer from 1 to 3; c is 1 to 3; d is 0 or 1; and the sum of c and d is at least 2.

4. A process of claim 3 wherein M is a Group 4 metal atom, wherein a is 0, wherein b is 1, and the sum of c and d is 3.

5. A process of claim 3 wherein M is a Group 4 metal atom, wherein b is 2 and the sum of c and d is 2.

6. A process of claim 1 wherein said metal compound is a metallocene represented by the formula:

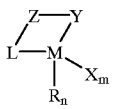

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group which does not detrimentally affect propagation of the polymer chain during polymerization, n is 1 to 4, m is 0 to 3, with the sum of n plus m being 1 to 4 depending upon the valence of M.

7. A process of claim 6 wherein M is a titanium, zirconium or hafnium atom, L is a cyclopentadienyl group or a substituted cyclopentadienyl group, Z is a dihydrocarbylsilyl group, Y is a hydrocarbylamido group, R is methyl, n is 2, and m is 0.

8. A process of claim 6 wherein M is a titanium or zirconium atom, L is a tetramethylcyclopentadienyl group, Z is a dimethylsilyl group, Y is a tert-butylamido group, R is methyl, n is 2, and m is 0.

9. A complex which comprises a cation formed from a d-block or f-block metal compound by loss of a leaving group and formation of an ion pair comprised of (a) said cation formed from a d-block or f-block metal compound and (b) a (polyfluoroaryl)fluoroanion of aluminum, gallium, or indium of the formula:

$$[ER'R''R'''F]^{\ominus}$$

wherein E is aluminum, gallium, or indium, wherein F is fluorine, wherein R' is a fluoroaryl group having at least one additional substituent other than fluorine, wherein R" and R'" each is, independently, (i) a fluoroaryl group having at least one additional substituent other than fluorine, or (ii) a fluorinated aryl group devoid of additional substitution.

10. A complex of claim 9 wherein the metal of said metal compound is a metal from Groups 4 to 8 of the Periodic Table.

11. A complex of claim 9 wherein the metal of said metal compound is thorium, titanium, zirconium, or hafnium.

12. A complex of claim 9 wherein said (polyfluoroaryl)fluoroanion is a weakly coordinating anion that has a coordinative ability essentially equivalent to or less than that of the corresponding (polyfluoroaryl)fluoroanion in which each substituent other than fluorine is replaced by a fluorine atom, when the coordinative abilities of the (polyfluoroaryl)fluoroanions are compared as salts of $[1,2-(9-fluorenyl)_2C_2H_4ZrMe]^{\oplus}$.

13. A complex of claim 9 wherein said (polyfluoroaryl)fluoroanion has a greater solubility in n-hexane at 20° C. than that of the corresponding (polyfluoroaryl)fluoroanion in which each substituent other than fluorine is replaced by a fluorine atom, and in which the counterion for each (polyfluoroaryl)fluoroanion is the same.

14. A complex of claim 9 wherein said (polyfluoroaryl)fluoroanion has the formula:

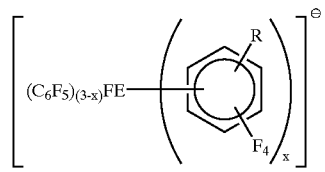

wherein E is aluminum, gallium, or indium, wherein F is fluorine, and wherein R is a substituent other than a fluorine atom, and x is from 1 to 3.

15. A complex of claim 9 wherein said (polyfluoroaryl)fluoroanion has the formula:

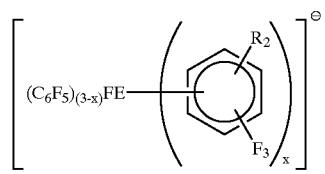

wherein E is aluminum, gallium, or indium, wherein F is fluorine, and wherein each R is, independently, a substituent other than a fluorine atom, and x is from 1 to 3.

16. A complex of claim 9 wherein at least one said additional univalent substituent of said (polyfluoroaryl)fluoroanion is an electron-withdrawing substituent.

17. A complex of claim 9 wherein at least one said additional univalent substituent of said (polyfluoroaryl)fluoroanion is an organic solvent solubility-enhancing substituent as determined in n-hexane at 20° C.

18. A complex of claim 9 wherein said metal compound is a metallocene represented by the formula:

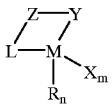

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group which does not detrimentally affect propagation of a polymer chain which is formed during polymerization, n is 1 to 4, m is 0 to 3, with the sum of n plus m being 1 to 4 depending upon the valence of M.

19. A complex of claim 18 wherein M is a titanium, zirconium, or hafnium atom, L is a cyclopentadienyl group or a substituted cyclopentadienyl group, Z is a dihydrocarbylsilyl group, Y is a hydrocarbylamido group, R is methyl, n is 2, and m is 0.

20. A complex of claim 18 wherein M is a titanium or zirconium atom, L is a tetramethylcyclopentadienyl group, Z is a dimethylsilyl group, Y is a tert-butylamido group, R is methyl, n is 2, and m is 0.

21. A complex of claim 9 wherein said metal compound is a metallocene represented by the formula:

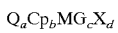

where Cp independently in each occurrence is a cyclopentadienyl-moiety-containing group which has in the range of 5 to about 24 carbon atoms; Q is a bridging group or ansa group that links two Cp groups together; M is a d- or f-block metal atom; each G is, independently, a leaving group that is bonded to the d- or f-block metal atom and is capable of being abstracted by an organocation of the organocation salt of the (polyfluoroaryl)fluoroanion used in forming the catalytic complex; X is a group other than a leaving group that is bonded to the d- or f-block metal atom and does not detrimentally affect propagation of a polymer chain which is formed during polymerization; a is 0 or 1; b is a whole integer from 1 to 3; c is 1 to 3; d is 0 or 1; and the sum of c and d is at least 2.

22. A complex of claim 21 wherein M is a Group 4 metal atom, wherein a is 0, wherein b is 1, and the sum of c and d is 3.

23. A complex of claim 21 wherein M is a Group 4 metal atom, wherein b is 2 and the sum of c and d is 2.

24. A process for preparing a catalytic complex or ion pair, which process comprises contacting a d-block or f-block metal compound having at least one leaving group with a salt of a (polyfluoroaryl)fluoroanion of aluminum, gallium, or indium of the formula:

[ER'R"R'"F]⊖ wherein E is aluminum, gallium, or indium, wherein F is fluorine, wherein R' is a fluoroaryl group having at least one additional substituent other than fluorine, R" and R'" each is, independently, (i) a fluoroaryl group having at least one additional substituent other than fluorine, or (ii) a fluorinated hydrocarbyl group devoid of additional substitution, in a suitably anhydrous liquid medium and in a suitably inert atmosphere or environment, such that a leaving group is abstracted from the d-block or f-block metal compound and an ion pair is formed, comprised of a cation formed from said d-block or f-block metal compound and said (polyfluoroaryl)fluoroanion.

25. A process of claim 24 wherein said metal compound is a metallocene represented by the formula:

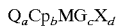

where Cp independently in each occurrence is a cyclopentadienyl-moiety-containing group which has in the range of 5 to about 24 carbon atoms; Q is a bridging group or ansa group that links two Cp groups together; M is a d- or f-block metal atom; each G is, independently, a leaving group that is bonded to the d- or f-block metal atom and is capable of being abstracted by an organocation of the organocation salt of the (polyfluoroaryl)fluoroanion used in forming the catalytic complex; X is a group other than a leaving group that is bonded to the d- or f-block metal atom and does not detrimentally affect propagation of a polymer chain which is formed during polymerization; a is 0 or 1; b is a whole integer from 1 to 3; c is 1 to 3; d is 0 or 1; and the sum of c and d is at least 2.

26. A process of claim 25 wherein M is a Group 4 metal atom, wherein a is 0, wherein b is 1, and the sum of c and d is 3.

27. A process of claim 25 wherein M is a Group 4 metal atom, wherein b is 2 and the sum of c and d is 2.

28. A process of claim 26 wherein said metal compound is a metallocene represented by the formula:

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group which does not detrimentally affect propagation of a polymer chain which is formed during polymerization, n is 1 to 4, m is 0 to 3, with the sum of n plus m being 1 to 4 depending upon the valence of M.

29. A process of claim 28 wherein M is a titanium, zirconium or hafnium atom, L is a cyclopentadienyl group or a substituted cyclopentadienyl group, Z is a dihydrocarbylsilyl group, Y is a hydrocarbylamido group, R is methyl, n is 2, and m is 0.

30. A process of claim 28 wherein M is a titanium or zirconium atom, L is a tetramethylcyclopentadienyl group, Z is a dimethylsilyl group, Y is a tert-butylamido group, R is methyl, n is 2, and m is 0.

* * * * *

UNITED STATES PATENT AND TRADEMARK OFFICE
CERTIFICATE OF CORRECTION

PATENT NO.   : 6,262,200 B1
DATED        : July 17, 2001
INVENTOR(S)  : Tobin J. Marks and You-Xian Chen It is certified that error appears in the above-identified patent and that said Letters Patent is hereby corrected as shown below:

Column 29,
Line 1, the first use of the word "or" should be deleted.

Column 32,
Line 33, claim dependency "26" should be -- 24 --.

Signed and Sealed this

Twenty-third Day of April, 2002

Attest:

Attesting Officer

JAMES E. ROGAN
Director of the United States Patent and Trademark Office